US006214205B1

(12) United States Patent
Willner et al.

(10) Patent No.: US 6,214,205 B1
(45) Date of Patent: Apr. 10, 2001

(54) DETERMINATION OF AN ANALYTE IN A LIQUID MEDIUM

(75) Inventors: Itamar Willner, Mevasseret Zion; Eugenii Katz, Jerusalem; Yael Cohen, Mevasseret Zion; Ron Blonder, Jerusalem, all of (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/117,256

(22) PCT Filed: Jan. 10, 1997

(86) PCT No.: PCT/IL97/00016

§ 371 Date: Dec. 15, 1998

§ 102(e) Date: Dec. 15, 1998

(87) PCT Pub. No.: WO97/27474

PCT Pub. Date: Jul. 31, 1997

(30) Foreign Application Priority Data

Jan. 26, 1996 (IL) .......................................... 116921

(51) Int. Cl.⁷ ..................................................... G01N 27/26

(52) U.S. Cl. ........................................ 205/777.5; 204/403

(58) Field of Search ........................... 204/403; 435/817; 205/777.5

(56) References Cited

U.S. PATENT DOCUMENTS

| | | | |
|---|---|---|---|
| 4,728,828 | 3/1988 | Goodnough | 327/434 |
| 4,822,566 | 4/1989 | Newman | 422/82.01 |
| 4,893,957 | 1/1990 | Byriel | 401/146 |
| 5,057,430 | 10/1991 | Newman | 435/287.2 |

FOREIGN PATENT DOCUMENTS

| | | |
|---|---|---|
| 1256944 | 7/1989 | (CA) . |
| 1259374 | 9/1989 | (CA) . |
| 0668502 | 8/1995 | (EP) . |

OTHER PUBLICATIONS

Ho et al. ("Amperometric detection of alkaline phosphatase activity at a horseradish peroxidase enzyme electrode based on activated carbon: potential application to electrochemical immunoassay", Biosenors & Bioelectronics, 10(1995) 683–391) Oct. 1995.*

Duan et al. ("Separation–Free Sandwich Enzyme Immunoassays Using Microporous Gold Electrodes and Self–Assembled Monolayer/Immobolized Capture Antibodies", Anal. Chem. 1994, 66, 1369–1377).*

Ngo, T.T., "(index of book) Electrochemical Sensors in Immunological Analysis" Plenum Press: New York and London (1987) MOnth unknown.

(List continued on next page.)

*Primary Examiner*—T. Tung
*Assistant Examiner*—Alex Noguerola
(74) *Attorney, Agent, or Firm*—Browdy and Neimark

(57) ABSTRACT

Electrochemical determination of the presence, and optionally concentration of an analyte utilizes an electrode having immobilized thereon one member of a recognition pair, the recognition pair consisting of said analyte. In the presence of the analyte medium pair complexes, which are complexes between the analyte and the immobilized member are formed. The electrode forms part of an electrochemical system which includes also redox molecules comprising at least one first redox molecule and at least one second redox molecule, the former transferring electrons between the electrode and the latter. Upon formation of a pair complex the electron transfer is inhibited and the change in the electrical response then indicates the presence of said analyte in the medium.

10 Claims, 25 Drawing Sheets

OTHER PUBLICATIONS

Bresler, H.S., et al. "Biosenser Design and Application," Mathewson, P.R., et al., Chapter 9 "Application of Capacitive Affinity Biosensors HIV Antibody and Glucose Detection," ACS Symposium Series 511, American Chemical Society: 89–104 (1992) Month Unknown.

Weber, S.G., et al., "Homogeneous Voltammetric Immunoassay: A Preliminary Study," *Analytical Letters* 12:1–9 (1979) Month Unknown.

Ngo, T.T., et al., "Electrochemical Sensors in Immunological Analysis," Doyle, M.J., et al., "Immunoassay in Differential Pulse Polarography and Anodic Stripping Voltammetry," Plenum Press, New York and London: pp. 87–102 (1987) Month Unknown.

Di Gleria, K., et al., "Homogeneous Ferrocene–Mediated Amperometric Immunoassay," *Anal. Chem.* 58:1203–1205 (1986) Month Unknown.

Di Gleria, K., et al., "Homogeneous Amperometric Ligand–Binding Assay Amplified by a Proteolytic Enzyme Cascade," *J. Electroanal. Chem.* 267:83–91 (1989) Month Unknown.

Chambers, J.A., et al., "The Development of Redox–Modified Electrodes as CHarge–Accumulating Devices for use in Higher Sensitivity Systems," *J. Electroanal. Chem.* 250:417–425 (1988).

Ngo, T.T., et al., "Electrochemical Sensors in Immunogical Analysis," Wright, D.S., et al., "Digoxin Homogeneous Enzyme Immunoassay with Amperometric Detection," Plenum Press, New York and London pp. 117–130 (1987) Month Unknown.

Tang, H.T., et al., "Electrochemical Enzyme Immunoassay for Phenytoin by Flow–Injection Analysis Incorporating a Redox Coupling Agent," *Clinical Chemistry* 37–2:245–248 (1991) Month Unknown.

Wehmeyer, K.R., et al., "Competitive Heterogeneous Enzyme Immunoassay for Gigoxin with Electrochemical Detection," *Anal. Chem.* 58:135–139 (1986) MOnth Unknown.

Ngo, T.T., et al., "Electrochemical Sensors in Immunological Analysis, " Aizawa, M. "Enzyme–Linked Immunosorbent Assays Using Oxygen–Sensing Electrode," Plenum Press, New York and London pp. 269–291 (1987) Month Unknown.

Franconi, C., et al., "Enzyme Immunoassay by Polarography—A Preliminary Study," *Journal Of Pharmaceutical& Biomedical Analysis* 5–3:283–287 (1987) Month Unknown.

Uditha de Alwis, W., et al., "Rapid Sub–Picomole Electrochemical Enzyme Immunoassay for Immunoglobu in G," *Anal. Chem.* 57:2754–2756 (1985) MOnth Unknown.

Tsuji, I., et al., "Enzyme Immunosensors Based on Electropolymerized Polytyramine Modified Electrodes," *Biosenors& Bioelectronics* 5:87–101 (1990) Month Unknown.

Ngo, T.T., et al., "Electrochemical Senors in Immunological Analysis," Gebauer, C.R., "Enzyme Immunoassay Using the Ammonia Gas–Sensing Electrode," Plenum Press, New York and London pp. 239–255 (1987) Month Unknown.

Niwa, M. et al., "Specific Binding of Concanaal in A to Glycolipid Monolayers on Gold Electrodes," *J. Chem. Soc., Chem. Commun.* pp. 547–549 (1992) Month Unknown.

Willner, I. et al., "Photoregulated Binding of Spiropyran-–Modified Concanaalin A to Monosaccharide–Funtionalized Self–Assembled Monolayers on Gold Electrodes," *J. Am. Chem. Soc.* 115:4937–4938 (1993).

Willner, I., et al., "Application of Photoisomerizable Antigenic Monolayer Electrodes as Reversible Amperometric Immunosensors, " *J. Am. Chem. Soc.* 116:9365–9366 (1994).

Riklin, A., et al., "Improving Enzyme–Electrode Contacts by Redox Modification of Cofactors," *Letters To Nature* 376:672–675 (Aug. 1995).

Langone, J.J., et al., "Methods in Enzymology, vol. 92, Immunochemical Techniques, Part E, Monoclonal Antibodies and General Immunoassay Methods," Morris , D.L., et al., "Colorimetric Immunoassays Using Flavin Adenine Dinucleotide as Label," Acad, Press, N.Y. pp. 413–425 (1983).

\* cited by examiner

MP = Val-Glu-Lys-Cys-Ala-Glu-Cys-His-Thr-Val-Glu-COOH ( microperoxidase MP-11 )

Electrocatalytic oxidation of glucose

No electrocatalytic oxidation of glucose

Electrocatalytic oxidation of glucose

Electrocatalytic oxidation of D-alanine

No electrocatalytic oxidation of D-alanine

Electrocatalytic oxidation of D-alanine

DETERMINATION OF AN ANALYTE IN A LIQUID MEDIUM

FIELD OF THE INVENTION

The present invention is generally in the field of assays for determination of the presence and optionally concentration of an analyte in a liquid medium. More specifically, the present invention concerns such an assay in which the analyte is determined by means of a change in the electrical response of an electrode which occurs in the presence of the analyte.

PRIOR ART

The prior art believed to be relevant as a background to the present invention consists of the following:
1. *Electrochemical Sensors in Immunological Analysis*, Ngo, T.T., Ed.; Plenum Press: New York and London, 1987.
2. Bresler, H. S.; Lenkevich, M. J.; Murdock, J. F.; Newman, A. L.; Roblin, R. O. in *Biosensor Design and Application*, Mathewson, P. R.; Finley, J. W., Eds.; ACS Symp. Ser. 511, Amer. Chem. Soc., Washington, D.C., 1992, pp.89–104.
3. U.S. Pat. No. 4,728,828.
4. U.S. Pat. No. 4,822,566.
5. U.S. Pat. No. 5,057,430.
6. U.S. Pat. No. 4,893,957.
7. Canadian Patent No. 1,256,944.
8. Canadian Patent No. 1,259,374.
9. Weber, S. G.; Purdy, W. C., *Anal Lett*. 1979, 12, 1–9.
10. Doyle, J. M.; Wehmeyer, K. R.; Heineman, W. R.; Halsall, H. B. in *Electrochemical Sensors in Immunological Analysis*, Ngo, T.T., Ed.; Plenum Press: New York and London, 1987, pp. 87–102.
11. Di Gleria, K.; Hill, H. A. O.; McNeil, C. J.; Green, M. J., *Anal. Chem.*, 1986, 58, 1203–1205.
12. Di Gleria, K.; Hill, H. A. O.; Chambers, J. A., *J. Electroanal. Chem.* 1989, 267, 83–91.
13. Chambers, J. A.; Walton, N. J., *J. Electroanal. Chem.* 1988, 250, 417–425.
14. Wright, D. S.; Halsall, H. B.; Heineman, W. R. in *Electrochemical Sensors in Immunological Analysis*, Ngo, T.T., Ed.; Plenum Press: New York and London, 1987, pp. 117–130.
15. Tang, H. T.; Halsall, H. B.; Heineman, W. R. *Clin. Chem.* 1991, 37, 245–248.
16. Wehmeyer, K. R.; Halsall, H. B.; Heineman, W. R.; Volle, C. P.; Chen, C., *Anal. Chem.* 1986, 58, 135–139.
17. Aizawa, M., in *Electrochemical Sensors in Immunological Analysis*, Ngo, T. T., Ed.; Plenum Press: New York and London, 1987, pp. 269–291.
18. Franconi, C.; Bonori, M.; Orsega, E. F.; Scarpa, M.; Rigo, A., *J. Pharm. Biomed. Anal.* 1987, 5, 283–287.
19. Uditha de Alwis, W.; Wilson, G. S., *Anal. Chem.* 1985,57,2754–2756.
20. Tsuji, I.; Eguchi, H.; Yasukouchi, K.; Unoki, M.; Taniguchi, I., *Biosens. Bioelectron.* 1990, 87–101.
21. Gebauer, C. R., in *Electrochemical Sensors in Immunological Analysis*, Ngo, T.T., Ed.; Plenum Press: New York and London, 1987, pp. 239–255.
22. Niwa, M.; Mori, T.; Nishio, E.; Nishimura, H.; Higashi, N., *J. Chem. Soc., Chem. Commun.* 1992, 547–549.
23. Willner, I.; Rubin, S.; Cohen, Y., *J. Amer. Chen. Soc.* 1993, 115, 4937–4938.
24. Willner, I.; Blonder, R.; Dagan, A., *J. Amer. Chem. Soc.* 1994, 116, 9365–9366.
25. European Patent Application, Publication No. 668,502.
26. Riklin, A.; Katz, C., Willner, I., Stocker A., Backmann, A. F., *Nature*, 1995, 376, 672.
27. Morris, D. L., Buckler, R. T., in *Methods in Enzymology*, V. 92, Part E (Eds. J. J. Langone, H., Van Vunakis), Acad. Press, N.Y. 1983, pp. 415–417.

BACKGROUND OF THE INVENTION

Owing to their specificity and high sensitivity, immunoassays are widely used in everyday clinical practice as well as in a variety of other applications such as environmental pollutant analysis and food quality analysis. Such assays are based on a specific binding between an antibody and an antigen.

Immunoassays based on electrochemical detection of binding have been a focus of considerable research and development activity (Ngo, T.T., Ed. 1987). In electrochemical immunoassay, what is detected is a change in electrical properties of an electrode solution interface as a result of antibody-antigen binding, such as changes in capacitance (Bresler, et al, 1992). Capacity affinity sensors have been disclosed in U.S. Pat. Nos., 4,728,822; 4,822,566 and 5,057, 430, U.S. Pat. No. 4,893,957 and Canadian Patent Nos. 1,256,944 and 1,259,374. Other electrochemical immunoassay methods are based on a change in the current or potential response as a result of formation of antigen-antibody complexes. Such methods require the presence of a redox probe attached to the antibody or antigen and the response of the electrochemical assay is a result of competitive binding between the analyte and the redox labeled antibody or antigen with the complementary member pair immobilized on the electrode. Such methods are not very sensitive and the amperometric detection of the redox-labeled molcule is limited to the micromolar range (Weber, et al., 1979; Doyle et al., 1987). More recent work has shown that by using a bare electrode and coupling the redox reaction with an enzymatic amplification system (Di Gleria et al, 1986; Di Gleria et al, 1988) there is improvement of the sensitivity. Use of a similar approach, but with an electrode modified with a redox polymer, resulted in an immunoassay that was more sensitive (Chambers, et al, 1988).

Another approach includes direct covalent coupling of antigen or antibody with biocatalytic molecules (usually redox enzymes) for amplification of the electrochemical signal. A number of studies have utilized amperometric or potentiometric detection of electro-active species such as NADPH (Wright, et al, 1987; Tang, et al, 1991), phenol (Wehmeyer, et al, 1986), $O_2$ (Aizawa, et al, 1987; Franconi, et al., 1987), $H_2O_2$ (Uditha, et al., 1985; Tsuji, et al, 1990), $NH_3$ (Gebauer, 1987), etc., generated analytically by an enzyme label on an antigen or antibody. The high sensitivity of this method makes it competitive with that of radioimmunoassay.

However, an electrical technique without any labeling of antigen/antibody species is even more attractive. Such methods are based on an amperometric detection of the permeability of redox molecules through a monolayer immobilized onto the surface of the electrode. An antigen monolayer provides much higher permeability to a solubilized redox probe than the same electrode reaction with an antibody with high binding affinity to the antigen (for illustration see FIG. 1) (Niwa, et al., 1992; Willner, et al, 1993; Willner et al, 1994; European Patent Application No. 668502).

GENERAL DESCRIPTION OF THE INVENTION

It is an object of the present invention to provide an electrochemical method and system for the determination of the presence and optionally concentration of an analyte in a liquid medium, the analyte being a member of a recognition pair.

It is furthermore an object of the invention to provide electrodes for use in such method and system.

Other objects of the invention will be clarified from the description below.

In the method and system of the invention, the presence of the analyte in the medium gives rise to a change in an electrical response. The term "electrical response" which will be used below denotes the current-voltage behavior of an electrode, e.g. the current response or the flow of charge of an electrode under a certain applied potential, etc. The electrical response may be determined by measuring current or charge flow, under alternating current or direct current conditions.

In the following the term "determine" or "determination" will be used to denote both determination of only the presence or determination of both the presence and concentration of an analyte in a liquid medium.

The electrical response in the method and system of the invention is a result of transfer of electrons between an electrode and an electron transfer chain formed by at least two redox molecules. The term "redox molecule" denotes a molecule which is capable of accepting or donating an electron thereby changing its redox state. The redox molecule may be an electron mediator capable of transferring electrons between an electrode and a redox molecule or between two redox molecules. The redox molecule may also be a catalytic molecule which upon change in its redox state becomes catalytically active following which it acts on a substrate which then changes into a chemically distinct product. A non-limiting example of a catalytically active redox molecule is a redox enzyme. In accordance with the invention, as will be further be explained below, when an analyte is present in a tested medium, an eventual result is impairment in the electron transfer change and accordingly a change in the electrical response of the electrode.

As noted above, the analyte which is being detected is an agent which is a member of a recognition pair, i.e. an agent which specifically binds to the other member of the pair to which it belongs. Recognition pairs are for example pairs of antigen-antibody, ligand-receptor, sugar-lectin, biotin-avidin, enzyme-substrate, oligonucleotide-oligonucleotide with complementary sequence, oligonucleotide-protein, and oligonucleotide-cell.

In the method and system of the invention, one of a recognition pair forms part of the assay system and is immobilized on an electrode. Exposure of the electrode to a medium comprising the analyte, which is the other member of the pair, brings to binding of the two to one another and consequently to association of the analyte onto the electrode.

The present invention provides by a first of its aspects, an electrochemical system for determining the presence of an analyte in a liquid medium, the system comprising:

redox molecules comprising at least one first redox molecule and at least one second redox molecule, said first redox molecule transferring electrons between said electrode and said second redox molecule; and an electrode having immobilized thereon one member of a recognition pair, said analyte being the other member of said pair, whereby presence of said analyte in the medium results in formation of a pair complex, being a complex between the immobilized member and said analyte;

formation of said pair complex inhibiting the electron transfer and a change in the system's electrical response as a result thereto, indicating presence of said analyte in the medium.

In accordance with one embodiment of the invention, the first and the second redox molecules are individual molecular entities, e.g. one immobilized on the surface of the electrode and the other freely tumbling in the surrounding medium. Alternatively, these two redox molecules may be complexed to one another, e.g. by means of a chemical linker molecule or, the complex may preferably be freely tumbling in the medium surrounding the electrode.

While a change in the electrical response indicates the presence of the analyte in the medium, the magnitude of change can optionally be used as a gauge for determining the concentration of the analyte in the medium. As will be appreciated, a larger concentration of the analyte will give rise to the formation of a large amount of pair complexes and thus to a larger change in the electrical response.

The present invention provides by another of its aspects an electrochemical method for determining presence of an analyte in a liquid medium, the method comprising:

a) providing an electrode having immobilized thereon one member of a recognition pair, said analyte being the other member of said pair; the electrode optionally having immobilized thereon a first redox molecule being capable of transferring electrons between the electrode and a second redox molecule;

b) contacting said electrode with said liquid medium, whereby the presence, therein of said analyte results in the formation of pair complexes, which are complexes between the immobilized member and said analyte, on the surface of said electrode;

c) contacting said electrode with said second redox molecule, and where said first redox molecule is not immobilized on said electrodes, also with said first redox molecule;

d) charging the electrode whereby electron transfer between said electrode and said second redox molecule by the mediation of said first redox molecule gives rise to an electrical response, a change in the electrical response following exposure of the electrode to said medium indicating the presence of said analyte in the medium.

The invention also provides an electrode useful in the above method and system.

The invention is useful for testing of analytes in a wide variety of media. These include body fluids, aquatic samples, food samples, etc. The analyte which is assayed may be an analyte originally present in the assayed medium, e.g. a hormone in a biological fluid; may be an analyte originally contained in a solid substrate, hidden within cells in a tissue, etc., and the sample containing the analyte is first treated to cause the analyte to dissolve into the assayed medium, etc. The analyte may also be a substance not originally present in the assayed media but comes into being as a result of a reaction involving another, and the determination of the analyte in such a case serves as an indirect measure for the determination of the other agent.

In the method and system of the invention, there is an electron transfer chain which consists of the electrode, and at least two redox molecules comprising said first and said second molecules. As pointed out above, it is possible, according to some embodiments of the invention for the two molecules to be linked to one another. When no analyte is present, the electrode has a thin monolayer which comprises the immobilized member, and there is thus substantially unhindered transfer of electrons along the chain. Once the analyte binds to the immobilized member and molecular complexes are formed on the surface of the electrode, there is a thickening of the monolayer and consequently an impairment in the electron transfer chain and a decrease in the electrical response of the electrode.

In accordance with one embodiment of the invention, said first redox molecule is a catalytically active molecule which upon transfer of electrons to the second redox molecule induces a reaction in which said second redox molecule is converted to one or more products.

In accordance with another embodiment of the invention, said first redox molecule is an electromediator and said second redox molecule is a catalytically active molecule. In accordance with this embodiment, there is provided also a third, substrate molecule which, in the electrocatalytic redox process is converted into a product. In this case, the electron chain comprises two redox molecules and a substrate.

In the above two embodiments, said first redox molecule may be immobilized on the electrode together with said immobilized member. In order to yield an electron transfer, the second redox molecule which is freely tumbling in the solution has to diffuse to and come into contact with the immobilized first redox molecule. Following exposure of the electrode to a medium comprising the analyte, pair complexes are formed on the surface of the electrode and the thickening of the monolayer on the surface of the electrode is a result thereto, so that there is a barrier for diffusion of the second redox molecule to the immobilized first redox molecule, yielding an impairment in the electron transfer chain.

In accordance with a further embodiment of the invention, the first and the second redox molecules are complexed: prior to binding of an analyte to the immobilized member, the complex can freely diffuse and come close enough to the surface of the electrode to allow electron transfer; once pair complexes are formed on the surface of the electrode, the redox complexes cannot reach the surface of the electrode and as a result there is impairment in the electron transfer and a reduction in the electrical response.

BRIEF DESCRIPTION OF THE DRAWINGS

FIG. 1 is a schematic representation of a prior art system, such as that described in European Patent Application Publication No. 668,502:

FIG. 2 is a general illustration of a system in accordance with an embodiment in which the electrode is a mixed monolayer containing the immobilized member together with an immobilized catalytically active redox molecule:

FIG. 3 is a general illustration of a system in accordance with another embodiment of the invention where the electrode carries a mixed monolayer comprising the immobilized member and an immobilized electron mediator redox molecule:

FIG. 4 is a general illustration of a system in accordance with another embodiment of the invention in which two redox molecules, one being an electron mediator molecule and the other a catalytically active redox molecule are complexed or bound to one another:

FIG. 5 illustrates the manner of modification of a cystamine covered gold electrode with a mixed monolayer consisting of 2,6-dinitrophenol lysine and microperoxidase:

FIG. 6 illustrates the function of the first redox molecule (MP) on electrodes obtained and in electrocatalytic reductions of the second redox molecule ($S_2O_s^{-2}$) as shown in FIG. 5:

FIG. 9 illustrates the function of a modified electrode obtained as shown in FIG. 8, where the first redox molecule, PQQ acts on an electrocatalyst for the oxidation of the second redox molecule, NADPH:

FIG. 13 illustrates the function of electrode obtained as shown in FIG. 12, with the ferrocene acting as the first redox molecule, glucose oxidase (GOD) as the second redox molecule and with glucose as the substrate:

FIG. 17 illustrates the functions of a system comprising an electrode as shown in FIG. 15 and an "electrically wired" GOD prepared as shown in FIG. 16.

FIG. 22 illustrates the function of a system comprising an electrode as shown in FIG. 15 and a reconstituted enzyme obtained as in FIG. 21.

FIG. 24 illustrates the function of a system comprising a modified electrode covered with a monocomponent 2,6-dinitrophenol lysine monolayer of FIG. 15 and D-alanine and D-amino acid oxidase (AAO) reconstituted with FAD-Fc.

DETAILED DESCRIPTION OF THE INVENTION

In the following, the invention will be described at times with reference to some non limiting specific embodiments illustrated in the annexed drawings. It will be understood that this specific description does not mean to impart any limitation on the scope of the invention but only to illustrate, by way of example the manner in which it may be carried out.

In accordance with the invention, an electrode is used which is covered by a monolayer comprising members of a binding couple which are immobilized thereon. The electrode is used for the determination of an analyte in a medium which is the other member of the binding couple which includes the immobilized member.

In accordance with some embodiments of the invention the immobilized layer on the electrode consists essentially of only immobilized members. In accordance with other embodiments of the invention, the layer of immobilized molecules on the surface of the electrode is a mixed layer comprising both said immobilized member and an immobilized redox molecule.

Figure 1A:
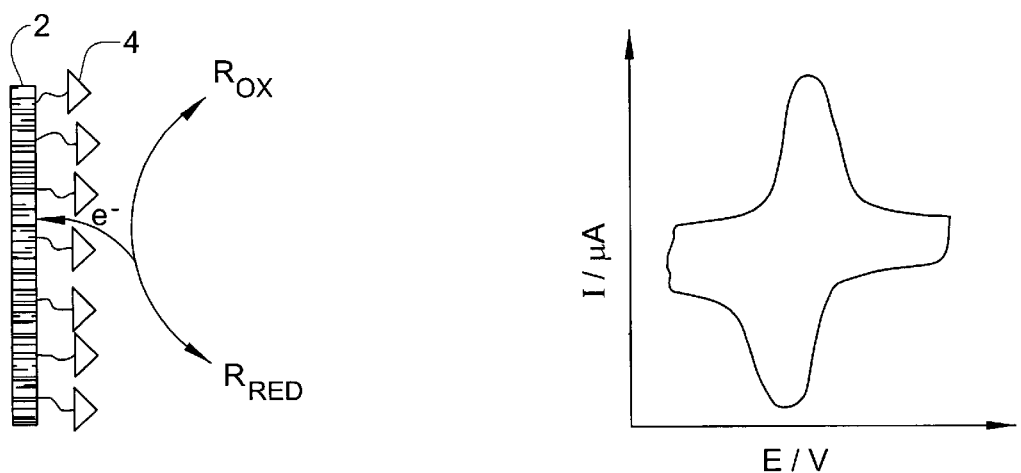
FIG. 1A illustrates the system and the electrical response prior to formation of pair complexes.

In order to appreciate the present invention, reference is first being made to FIG. 1 illustrating a system in accordance with the prior art such as that described in European Patent Application No. 668,502. In this system an electrode 2 is covered by a monolayer consisting of a plurality of immobilized members 4. The system further comprises redox molecules (R) which can either be in an oxidized state (Rox) or in a reduced state (Rred). When the electrode is energized, electrons ark transferred between the electrode and the redox molecule and depending on the type of transfer of the electrons, the system progresses in an oxidation or reduction pathway. The electrical response of the electrode is shown schematically in the right.

Figure 1B:
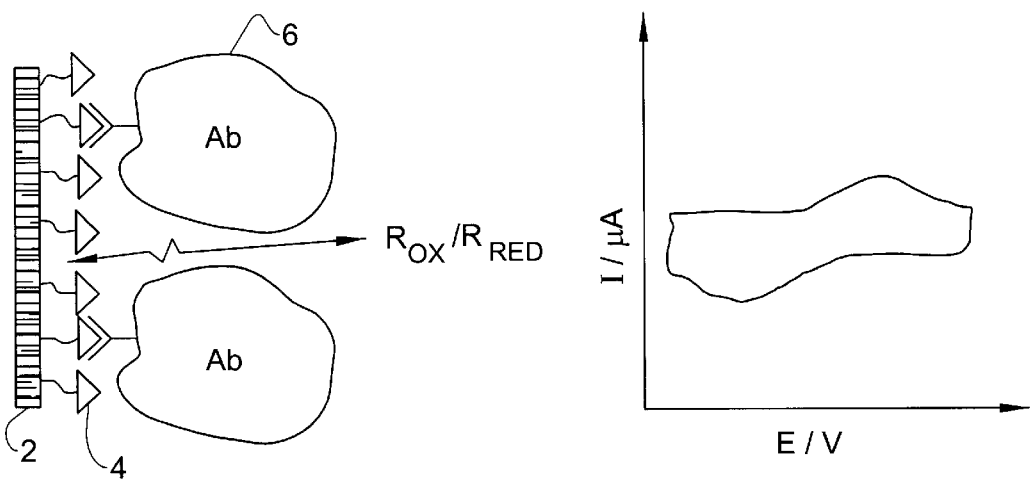
FIG. 1B illustrates the system and the electrical response after formation of pair complexes.

Upon exposure of the electrode to an analyte containing medium, the analyte in this example being antibody 6 as shown in FIG. 1B, immobilized pair complexes are formed on the electrode which thicken the immobilized monolayer and inhibit diffusion of the redox molecules to the surface of the electrode. Because of this impaired diffusion, there is a smaller electrical response as can be seen schematically in the right. In this prior art system, the change of electron transfer involves one transfer step between the electrode and a redox molecule. As distinct therefrom, in accordance with the invention, the electron transfer pathway comprises at least two electron transfer steps. This longer chain of electron transfer increases sensitivity and reduces inaccuracies as a result of imperfect immobilized monolayer structure. The increased sensitivity of the invention is particularly manifested where one of the redox molecules is immobilized on the electrode and the other is a relatively large molecule with a relatively high molecular weight.

The general advantage of the method in accordance with the invention is in that there is a marked amplification, as compared to the prior art, in the signal-to-background ratio.

Figure 2A:
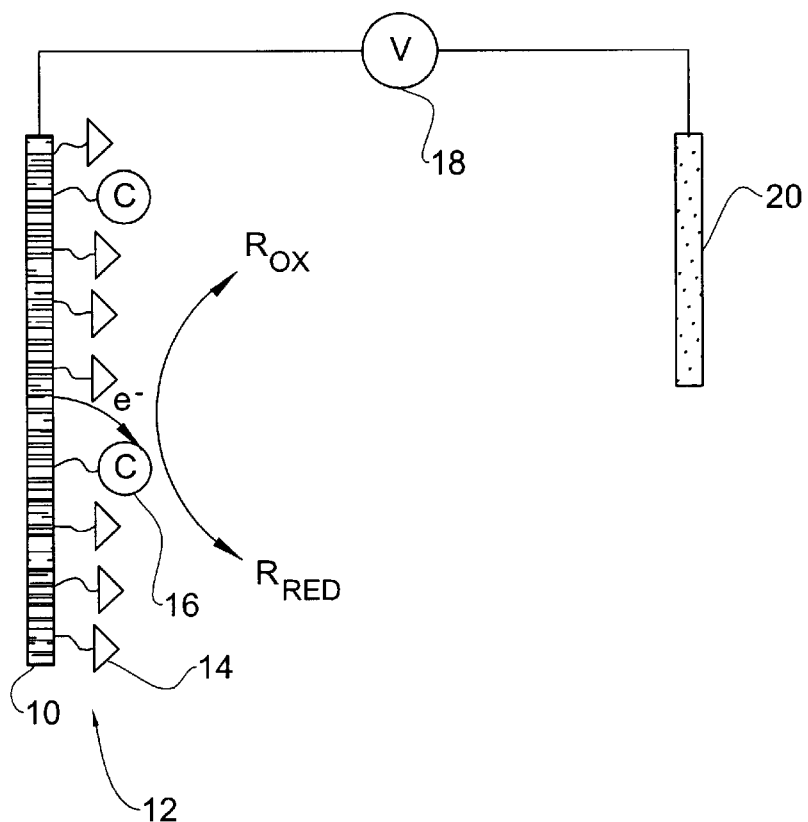
FIG. 2A shows a system prior to exposure to an analyte.

A schematic illustration of one preferred embodiment in accordance with the invention is shown in FIG. 2. In accordance with this embodiment, an electrode 10 has immobilized thereon a monolayer 12 comprising immobilized members 14 and a catalytic redox molecule 16. A catalytic molecule 16 is capable of exchanging electrons with the electrode 10 thereby changing its redox state. Upon change in its redox state, it becomes catalytically active whereupon it induces a change in the redox state of redox molecule R. The electrode 10 forms part of an electrical circuit comprising a power source 18 and a counter electrode 20. In addition, as customary in electrochemical systems, the system typically comprises also a reference electrode, e.g. a saturated calomel electrode (not shown).

Figure 2B:
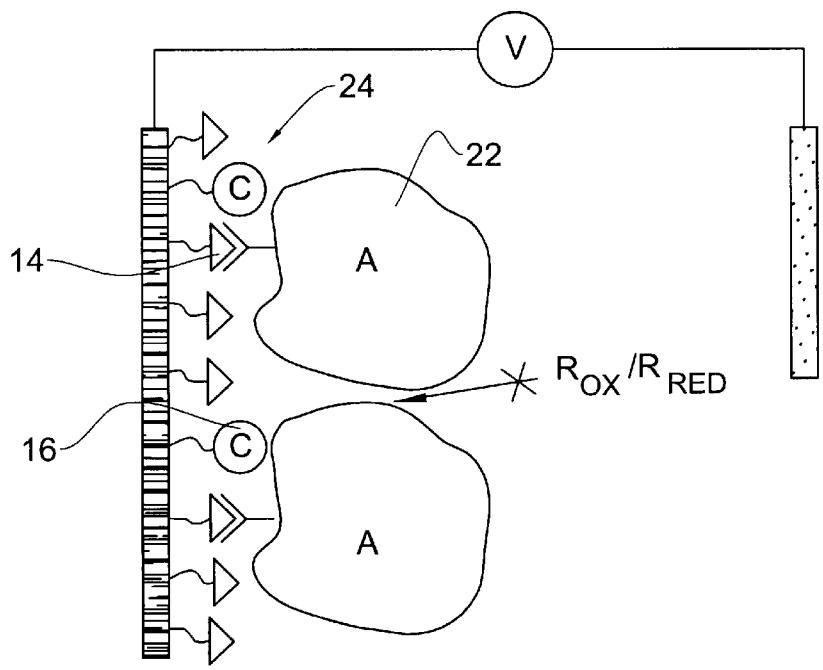
FIG. 2B shows a system after exposure to the analyte and formation of pair complexes.

FIG. 2B shows the system after exposure of the electrode to analyte molecules 22, which may for example be an antibody, which upon binding brings to the formation of immobilized pair complexes 24 which provide a barrier for diffusion of redox molecules towards the immobilized catalytic redox molecule 16. Consequently, there is impairment in the electron transfer chain and a marked reduction in the electrical response of the system. However, as there are some "pin-holes" in the monolayer, some diffusion of the redox to the surface of the electrode is possible and accordingly some electrical response remains even after saturated binding of analytes 22 to the immobilized member 14.

Figure 3A:
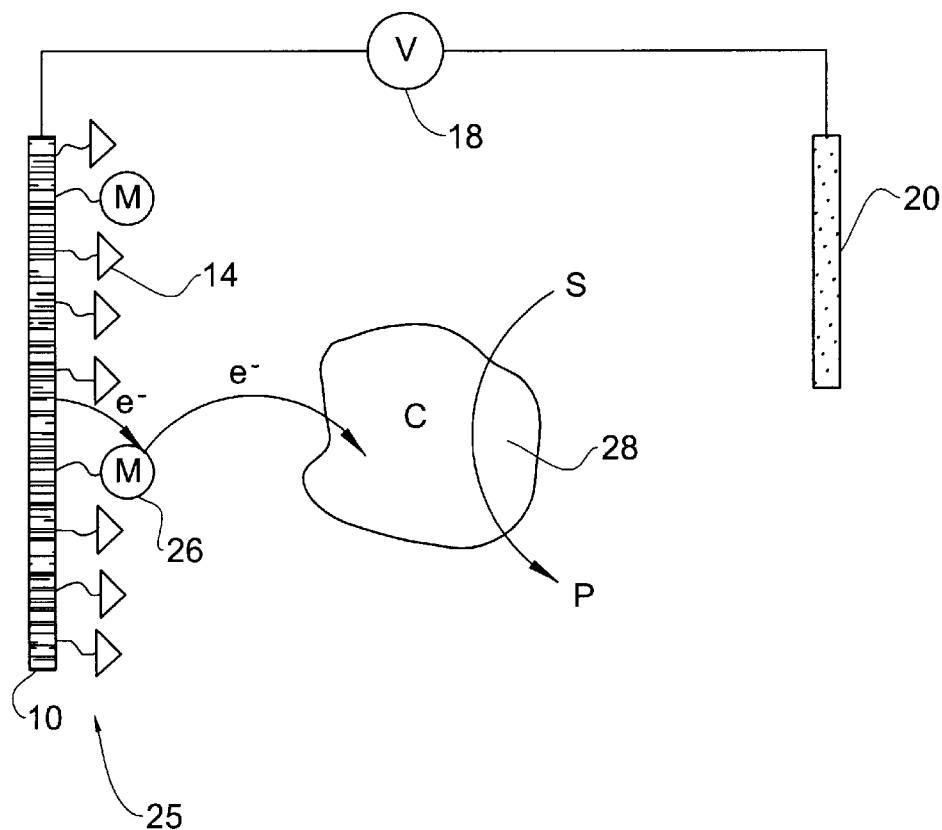
FIG. 3A illustrates the system prior to exposure to the analyte.
Figure 3B:
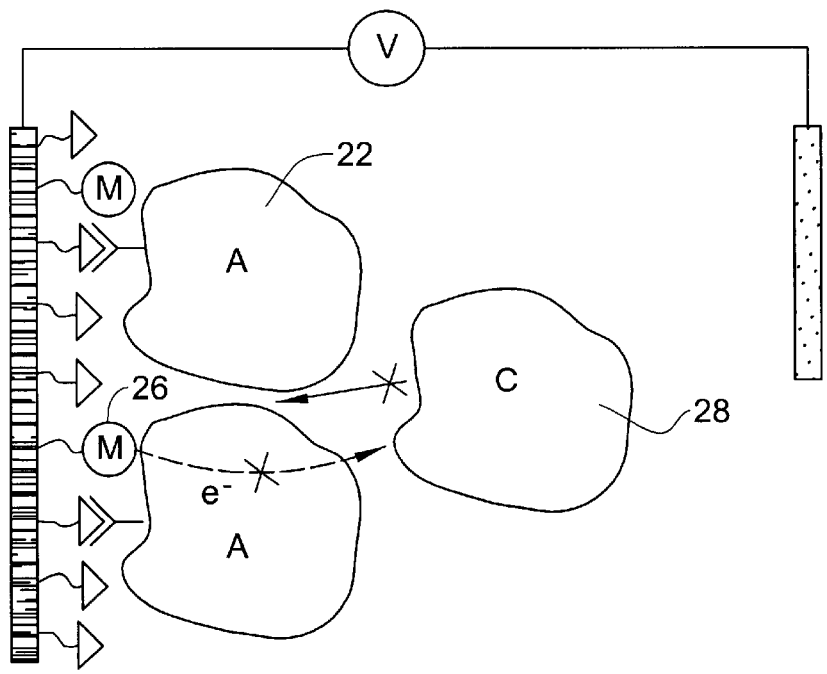
FIG. 3B illustrates the system after exposure to the analyte and formation of pair complexes.
Figure 4A:
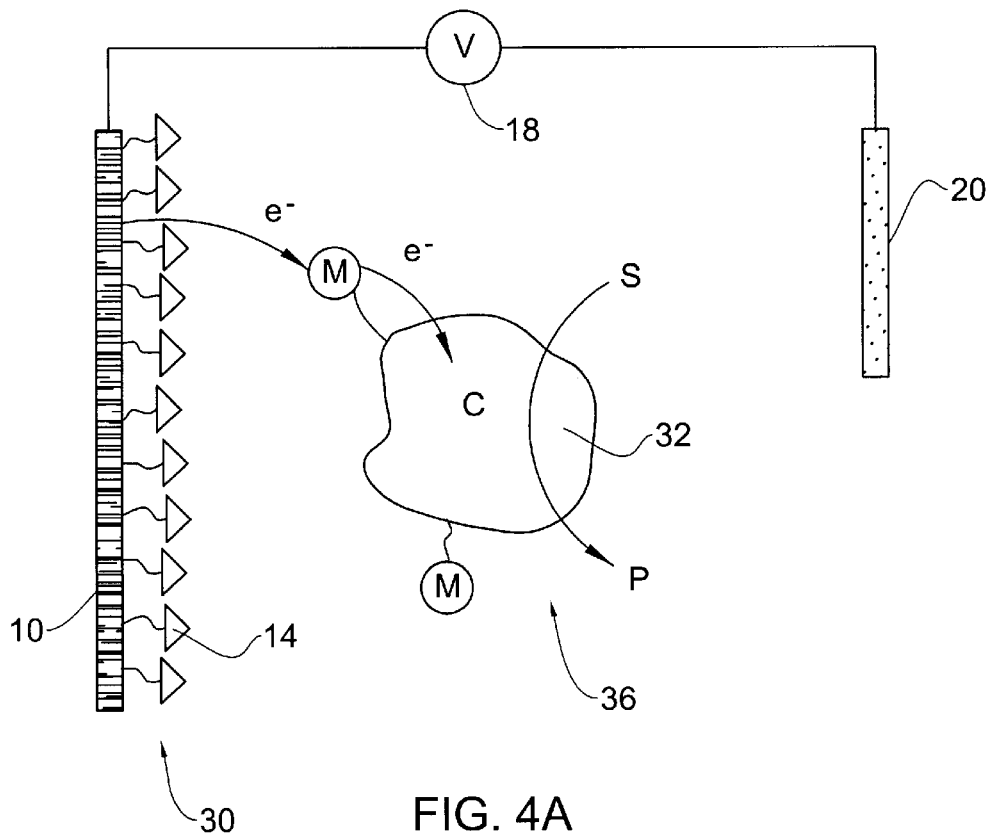
FIG. 4A illustrates the system prior to exposure to the analyte.

In FIGS. 3 and 4, two other preferred embodiments are described. For ease of description, like elements in these embodiments have been given like numerals to those used in FIG. 2 and the reader is referred to the description of FIG. 2 for explanation of the function of the respective components.

In the system of the embodiment of FIG. 3, the monolayer 25 immobilized on the surface of electrode 10 comprises immobilized members 14 and electron mediator redox molecules 26. Mediator molecules 26 are capable of transferring electrons between electrode 10 and a soluble catalytically active redox molecule 28, which may for example be an enzyme. Upon energizing of electrode 10, electrons are transferred between the electrode and molecule 28 and consequently molecule 28 catalyzes a reaction in which a substrate S is converted into a product P or vice versa (depending on the direction of the redox reaction).

Proper electron transfer depends on diffusion of molecule 28 towards the surface of the electrode so as to come into proximity with electrode mediator molecule 26. Upon binding of analyte molecules 22 and the formation of pair complexes, given the size, the free diffusion of molecule 28 towards the surface of the electrode is impeded and consequently there is impairment in the electron transfer and a marked reduction in the electrical response of the system to almost zero.

Reference is now made to FIG. 4. In this embodiment, monolayer 30 on electrode 10 comprises essentially only immobilized member 14. Catalytically active molecule 32 is bound or complexed to electron mediator redox molecule 34 which together form complex 36. When complex 36 approaches the surface of electrode 10, electron mediator molecule 34 is capable, upon energizing of the electrode, of transferring electrons between electrode 10 and the catalytic center of molecule 32. Upon change in the redox state, molecule 32, which may for example be an enzyme, catalyzes a reaction in which substrate is compared into a product or vice versa.

Figure 4B:
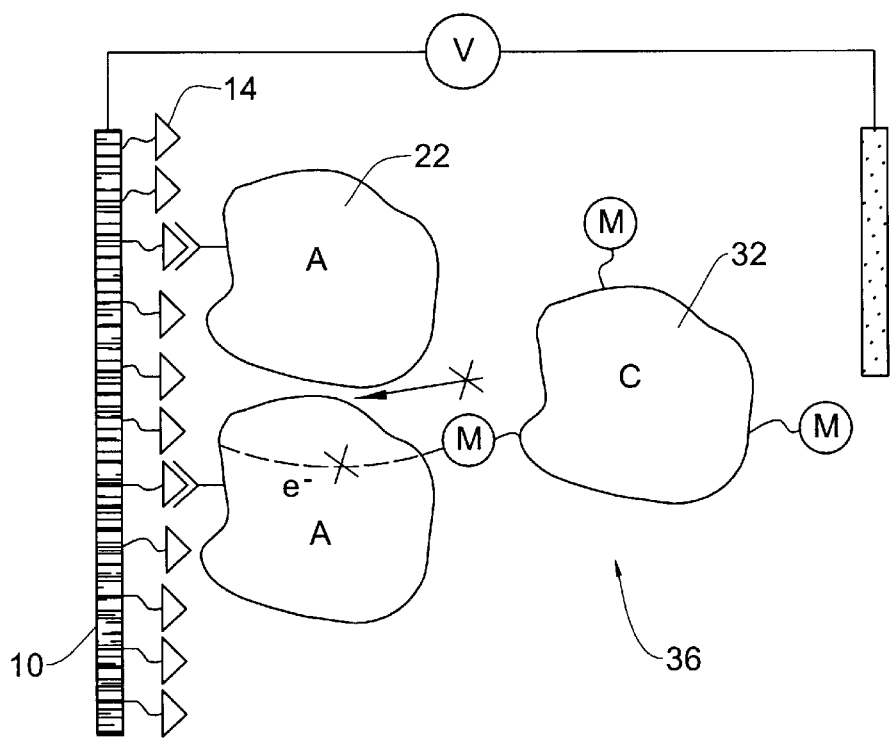
FIG. 4B illustrates the system after exposure of the electrode to the analyte and formation of pair complexes.

Upon binding of analyte molecules 22 to the immobilized members 14, as shown in FIG. 4B, the diffusion of complex 36 towards the surface of the electrode is inhibited and accordingly there is an impairment in the transfer of electrons between electrode 10 and molecule 32 and hence a reduction in the electrical response of the system.

The electrical response of the system may be determined directly by charging the electrode with the appropriate potential, and alternatively, by a variety of electrochemical methods such as cyclic voltammetry, chronoamperimetry, etc. However, it is also possible to measure the electrical response by other means, e.g. measuring the charge flow. Furthermore, where the reaction yields a formation of a product, it is possible at times to indirectly determine the electrical response by measuring the rate of product accumulation.

The electrode may be made of or coated by an electrically conducting substance, such as gold, platinum, silver, conducting glass such as Indium tin oxide (ITO) with functionalized alkoxysilane on the external surface (silanization of an ITO electrode may, for example, be by refluxing the electrode in an argon atmosphere with 3-aminopropyltriethoxysilane in dry toluene and then drying in an oven).

The immobilized member or an immobilized redox molecule may be immobilized on the surface of the electrode by means of a linking group, which typically may have the following general formula (I):

wherein:

(1) Z in case where the electrode material is one of the above-mentioned metals, 2 represents a sulphur-containing moiety which is capable of chemical association with, attachment to or chemisorption onto said metal; and in case where the electrode material is glass, represent methoxy or alkoxy silane residues which are capable of chemical association, attachment to or chemisorption onto said glass;

$R^1$ represents a connecting group;

Q is a functional group which is capable of forming a covalent bond with a moiety in the immobilized member or in said first redox molecule.

(2) Z where the electrode material is a metal may for example be a sulphur atom, obtained from a thiol group or a disulfide group, a sulphonate or sulphate groups.

$R^1$ may be a covalent bond or may be a peptide or polypeptide or may be selected from a very wide variety of suitable groups such as alkylene, alkenylene, alkynylene phenyl containing chains, and many others.

Particular examples of $R^1$ are a chemical bond or a group having the following formulae (IIa), (IIb), (IIc) or (IId)

$$-R^2-\overset{\overset{A'}{\|}}{C}- \qquad (IIa)$$

$$-R^2-NH- \qquad (IIb)$$

$$-R^2-N=CH-R^3-\overset{\overset{A}{\|}}{C}- \qquad (IIc)$$

$$-R-NH-\overset{\overset{A}{\|}}{C}-NH-Ph-CH=CH-Ph-NH-\overset{\overset{B}{\|}}{C}- \qquad (IId)$$

wherein $R^2$ or $R^3$ may be the same or different and represent straight or branched alkylene, alkenylene, alkynylene having 1–16 carbon atoms or represent a covalent bond, A and B may be the same or different and represent O or S, Ph is a phenyl group which is optionally substituted, e.g. by one or more members selected from the group consisting of $SO_3$— or alkyl groups.

Q may, for example, be a functional group capable of binding to a carboxyl residue of a member of a recognition pair such as an amine group, a carboxyl group capable of binding to an amine residue of the member of a recognition pair; an isocyanate or isothiocyanate group or an acyl group capable of binding to an amine residue of the member of a recognition pair; or a halide group capable of binding to hydroxy residues of the protein or a polypeptide. Particular examples are the groups —$NH_2$—COOH; —N=C=S; N=C=O; or an acyl group having the formula —$R^a$—CO—G wherein G is hydrogen, a halogen such as Cl, or is OH, $OR^b$, a $$-O\overset{\overset{O}{\|}}{C}-R^b$$

independently a $C_1$–$C_{12}$ alkenyl, alkenyale or a phenyl containing chain which is optionally substituted, e.g. by halogen.

Particular examples of linking groups are those of the following formulae (III)–(VII):

$$HS-(CH_2)_{\overline{n}}-NH_2 \qquad (III)$$

$$\begin{array}{l} S-(CH_2)_{\overline{n}}-NH_2 \\ | \\ S-(CH_2)_{\overline{n}}-NH_2 \end{array} \qquad (IV)$$

$$HS-(CH_2)_{\overline{n}}-N=CH-(CH_2)_n \qquad (V)$$

$$\begin{array}{l} S-(CH_2)_{\overline{n}}-\overset{\overset{O}{\|}}{C}-O-N \\ | \\ S-(CH_2)_{\overline{n}}-\overset{\overset{}{\|}}{\underset{\underset{O}{\|}}{C}}-O-N \end{array} \qquad (VI)$$

$$S-(CH_2)_{\overline{n}}-\overset{\overset{O}{\|}}{C}-O-N \qquad (VII)$$

where n is an integer between 1–6.

The sensitivity of the system of the invention may be increased by the use of analyte molecules which are conjugated or complexed with a large molecule or a group of molecules (hereinafter at times "complexed analyte"). By binding to the immobilized member, the complexed analytes sterically impede access of redox molecules to the electrode material. In one embodiment, this is achieved by the use of analytes conjugated to a large molecule or complex of molecules, such as for example, an anti-antibody to an analyte antibody, an antibody to a protein analyte, and the like.

In another embodiment, after the analyte is allowed to bind to the immobilized member, the electrode is challenged with agents capable of binding to the bound analyte, whereby the agents complexed with the bound analyte give rise to steric impedance. In order to increase the steric impedance, after the formation of an initial complex, the electrode is reacted with anti-agents which bind or are complexed to the agents already bound or complexed to the immobilized analyte, e.g. an anti-antibody and this brings about an increase in the size of the complex and hence also an increase in the steric impedance.

By increasing the sensitivity of the system in the manner described above, a change in the electrical response of the electrode can at times be measured after binding of only a few analyte molecules to the electrode.

EXAMPLES

The invention will now be further illustrated in the following examples. In these examples the electrodes were covered with a monolayer comprising the antigen dinitrophenyl (DNP) to which were then bound anti-DNP antibodies. It will be appreciated that this is an example only of a myriad of antigens which can be immobilized on the surface of the electrode. Furthermore, it is clear that the antibody-antigen recognition pair is also an example of a variety of other such pairs which can be utilized in accordance with the invention, one of which is immobilized on the electrode and the other is the assayed analyte.

The same above general statement is true also with respect to all the other specific reagents, enzymes, catalysts, redox molecules, etc. shown in the specific embodiments below.

1. ELECTRODE CHARACTERIZATION AND ELECTROCHEMICAL SET-UP

A gold electrode (0.5 mm diameter Au wire of geometrical area ca. 0.2 $cm^2$) was used for all modifications and measurements. A cyclic voltammogram recorded in 0.5 M $H_2SO_4$ was used to determine the purity of the electrode surface just before modification. The real electrode surface area and coefficient of roughness (ca. 1.1) were estimated from the same cyclic voltammogram by integrating the cathodic peak for the electrochemical reduction of the oxide layer on the electrode surface.

Electrochemical measurements were performed using a potentiostat (EG&G VersaStat) connected to a personal computer (EG&G research electrochemistry software model 270/250). All the measurements were carried out in a three-compartment electrochemical cell comprising the chemically modified electrode as a working electrode, a glassy carbon auxiliary electrode isolated by a glass frit and a saturated calomel electrode (SCE) connected to the working volume with a Luggin capillary. All potential are reported with respect to this reference electrode (the SCE). Argon bubbling was used to remove oxygen from the solutions in the electrochemical cell. During the measurements the temperature of the cell was controlled by circulated water in a jacket around the cell.

2. PRELIMINARY STEPS IN ELECTRODE MODIFICATION 2.1 Cleaning of an electrode surface To remove the previous organic layer and to regenerate a bare metal surface, the electrode was treated by boiling it in a 2 m KOH solution for 1 hour, then rinsed with water and stored in concentrated sulfuric acid. Immediately prior to further modification, the electrode was rinsed with water, soaked for 10 min. in concentrated nitric acid and then rinsed again with water.

2.2 Electrode modification with cystamine

Figure 15:
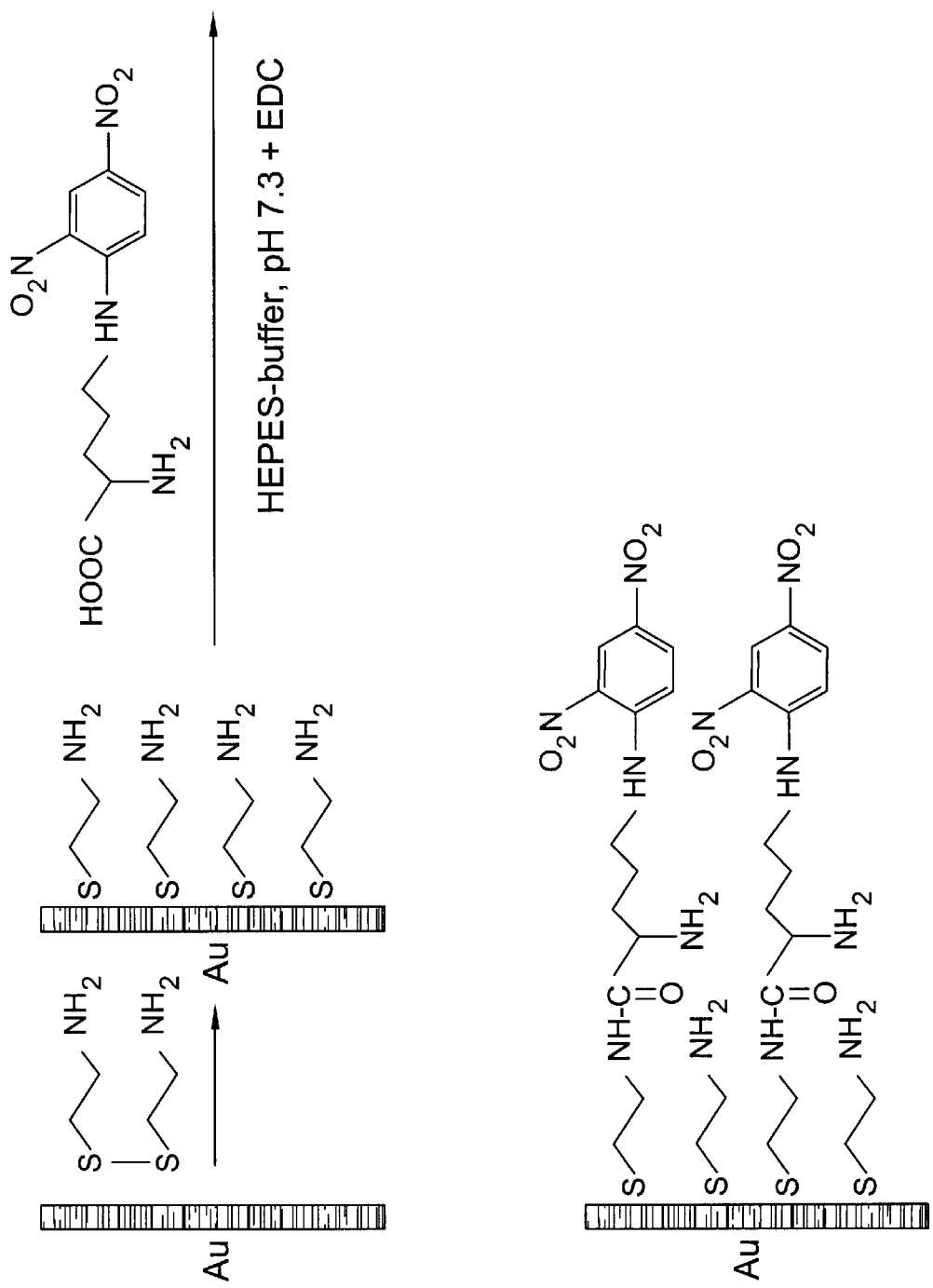
FIG. 15 illustrates the manner of modification of a gold electrode to obtain a monocomponent 2,6-dinitrophenol lysine monolayer.

A clean bare gold electrode was soaked for 2 hours in a solution of 0.02 M cystamine (2,2'-diaminodiethyldisulfide, Aldrich) in water (see first step in the procedure illustrated in FIG. 15). The electrode was then rinsed thoroughly with water to remove excess cystamine.

Figure 5A:
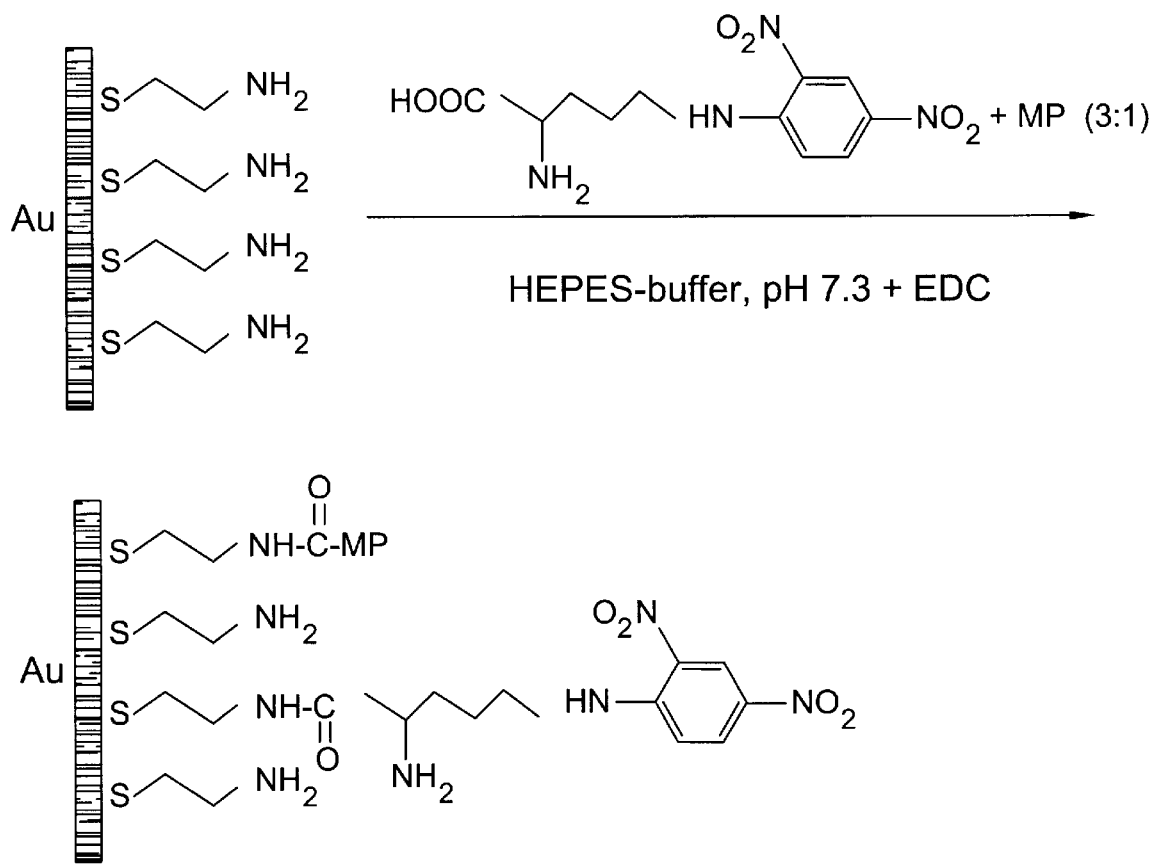
FIG. 5A illustrates the sequence of modification.
Figure 5B:
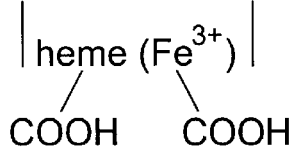
FIG. 5B illustrates the structure of microperoxidase (MP).

3. ELECTRODES WITH A MIXED MONOLAYER CONSISTING OF AN ANTIGEN COMPONENT AND A CATALYST (ELECTRON TRANSFER MEDIATOR) COMPONENT 3.1 Dinitrobenzene derivative as an antigen and microperoxidase as a catalyst A gold electrode modified so as to have a cystamine monolayer was soaked for 1 hour in a 0.01 M HEPES buffer solution, pH 7.3, containing 3 mM 2,6-dinitrophenyl lysine (as an antigen), 1 mM of the catalyst microperoxidase MP-11 (Aldrich) and 10 mM 1-ethyl-3-(3-dimethylaminopropyl) carbodiimide (EDC, Aldrich), serving as a coupling reagent. Then the modified electrode was thoroughly rinsed with water to remove from its surface uncoupled physically adsorbed components. The modification scheme is illustrated in FIG. 5. A cyclic voltammogram was taken in the potential window from 0 V to −0.6 V with a potential scan rate 0.1 V s$^{-1}$, and the electrochemically reversible redox process of the immobilized microperoxidase was used to determine its surface density on the electrode surface. The obtained value of about $3 \cdot 10^{-11}$ was approximately half that obtained with a monocomponent monolayer formed by microperoxidase alone.

Figure 6A:
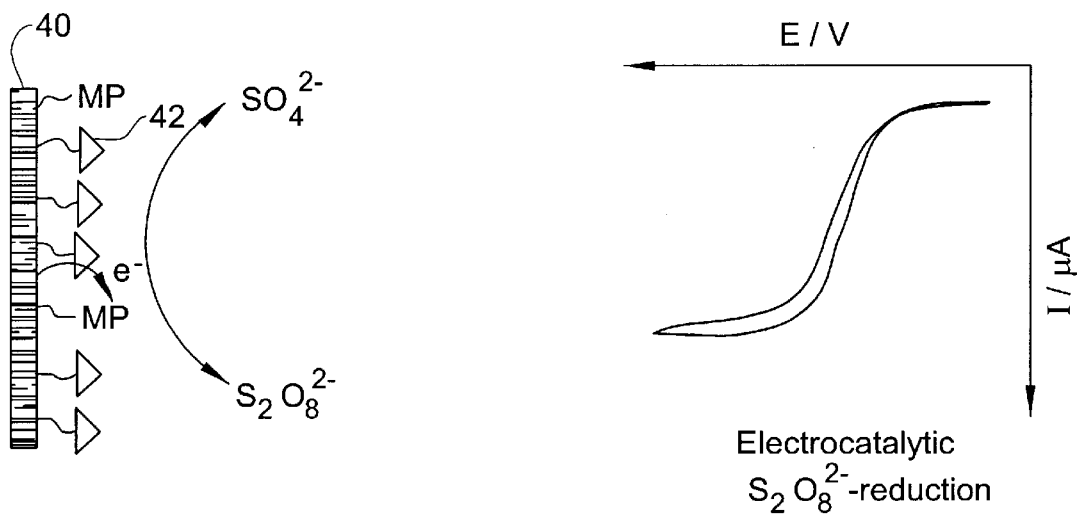
FIG. 6A illustrates the function and schematic representation of the current response of the electrode prior to exposure to antibodies.
Figure 6B:
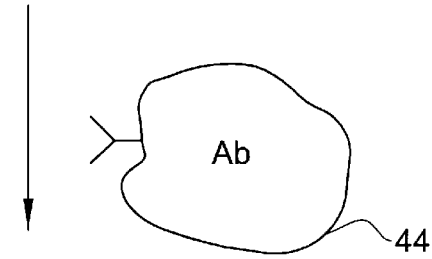
FIG. 6B illustrates the system and schematic representation of the current response of the electrode after exposure to antibodies and formation of pair complexes.
Figure 6B:
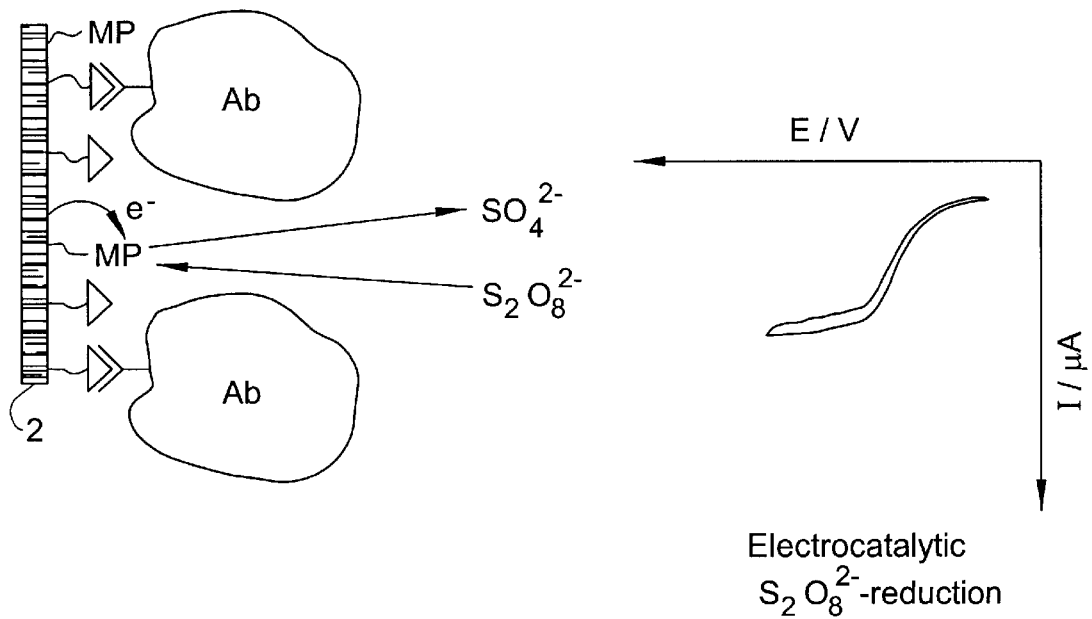

The functioning of the obtained electrode can be seen in FIG. 6. The electrode 40 comprises immobilized 2,6-dinitrophenyl lysine molecules 42 (the triangle represents the dinitrophenyl (DNP) moiety) and microperoxidase (MP) molecules. When the electrode 40 is energized, electrons are transferred to the MP molecule and consequently the MP molecule catalyzes the reduction of $S_2O_s^{-2}$ into $SO_4^{-2}$. When the electrode is then exposed to an anti-DNP antibody 44 which binds to the immobilized DNP moieties on the electrode, as can be seen in FIG. 6B, the monolayer on the surface of the electrode thickens, thus inhibiting the diffusion of the $S_2O_s^{-2}$ and the $SO_4^{-2}$ to and from the immobilized MP molecules, respectively. As a result, after binding of the antibodies, there is a reduction in the electrical response of the system.

Figure 7:
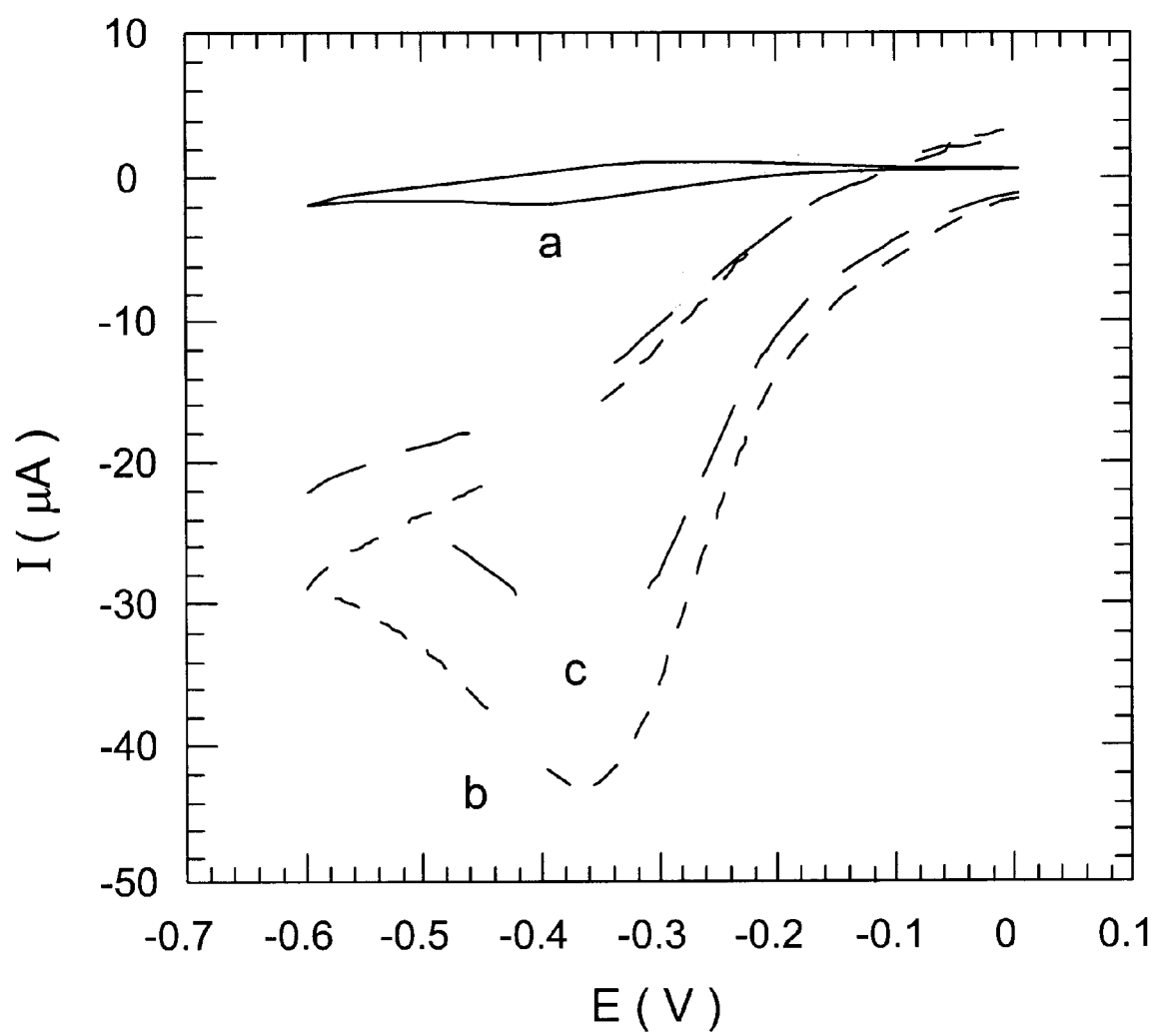
FIG. 7 shows cyclic voltammograms obtained with a modified gold electrode of a kind shown in FIGS. 5 and 6:
(a) in a control solution comprising 0.01 M phosphate buffer, pH 7.0 and 0.1 M $Na_2SO_4$;
(b) in the presence of 50 mM $K_2S_2O_8$;
(c) in the same solution after 20 mins. incubation of the modified electrode in a solution comprising 50 mg/ml anti-dinitrophenol antibodies. Potential scan rate −10 mv/s; temperature −25° C.

Cyclic voltammograms obtained in this system, (at 25° C.) are shown in FIG. 7. Curve b shows the cyclic voltammogram obtained in the presence of 50 mM $K_2S_2O_s$ (subsequently electrically reduced by microperoxidase), 0.01 M phosphate buffer and 0.1 M $Na_2SO_4$. Curve a, in comparison, shows a cyclic voltammogram taken in the absence of $K_2S_2O_s$. The considerable increase in the cathodic current between curve a and curve b is a result of the electrocatalytic reduction of $K_2S_2O_s$. Curve c shows a cyclic voltammogram obtained under the same condition as cyclic voltammogram of curve b but after soaking of the electrode for 20 min. in a solution containing 50 mg/ml DNP antibody (monoclonal mouse IgE anti-DNP, Sigma, St. Louis) and then rinsing with water to remove excess antibodies. The significant decrease in the electrocatalytic cathodic current results from the blocking effect of the antibody bound to the electrode's surface.

In control experiments, a non specifically adsorbed protein, such as albumin, or with an electrode coated with the microperoxidase only (without the antigen), did not yield any decrease in the cathodic current following exposure to the anti-DNP antibodies.

Figure 8:
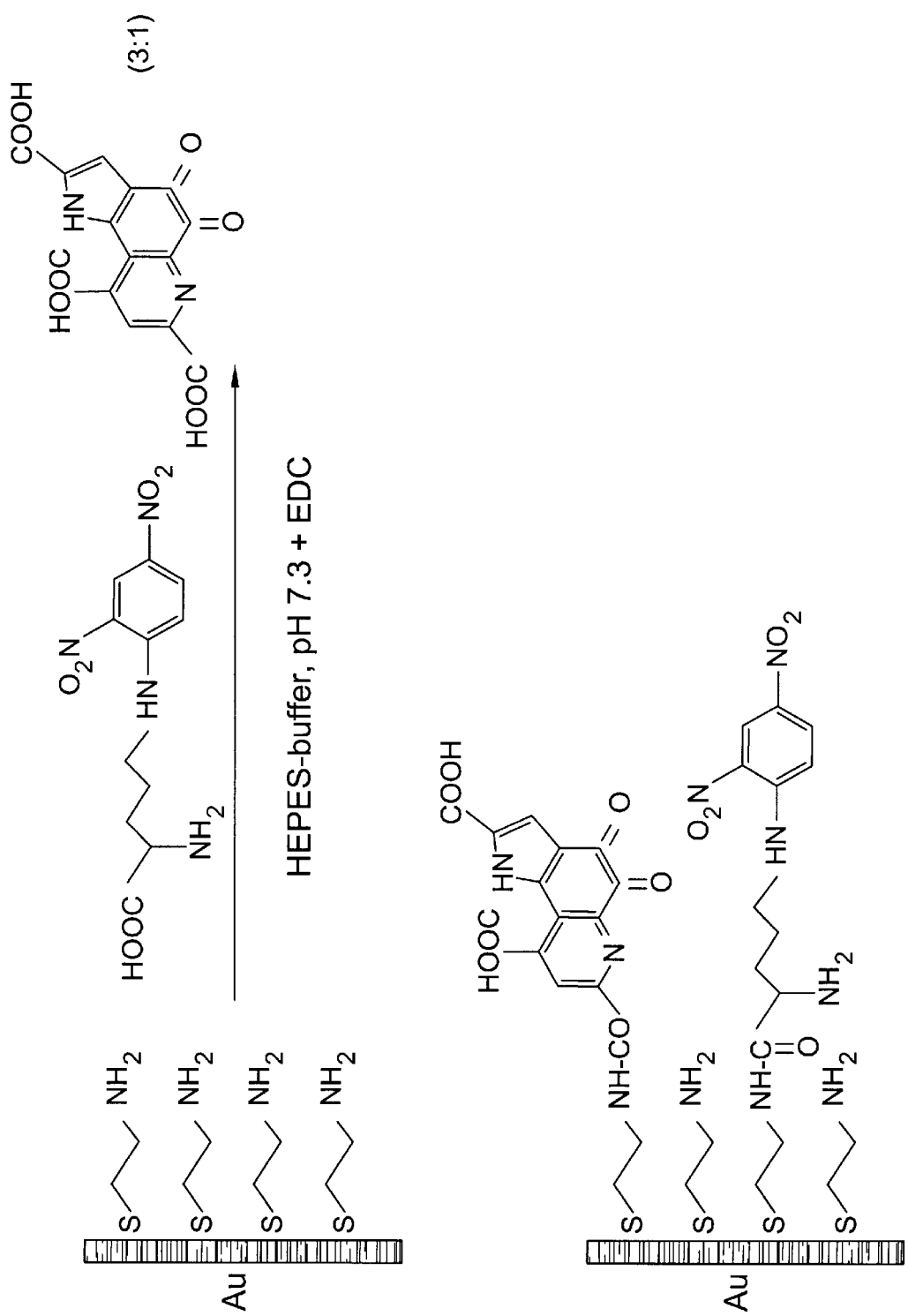
FIG. 8 illustrates the manner of modification of a cystamine covered gold electrode with a mixed monolayer consisting of 2.6-dinitrophenol lysine and PQQ.

3.2 Dinitrobenzene derivative as an antigen and pyrroloquinoline quinone as a catalyst A gold electrode modified so as to have a cystamine monolayer was soaked for 3 hours in a 0.01 M HEPES buffer solution, pH 7.3, containing 3 mM 2,6-dinitrophenol lysine (Aldrich) (as an antigen), 1 mM of the catalyst pyrroloquinoline quinone (PQQ) (Aldrich) and 10 mM 1-ethyl-3-(3-dimethylaminopropyl) carbodiimide (EDC, Aldrich), as a coupling reagent) Then the modified electrode was thoroughly rinsed with water to remove from its surface uncoupled physically adsorbed components. The modification scheme is illustrated in FIG. 8. A cyclic voltammogram was taken in the potential window from +0.1 V to −0.5 V with a potential scan rate 0.05 V s$^{-1}$ and the electrochemically reversible redox process of the immobilized PQQ was used for determination of its surface density on the electrode surface. The obtained value of about $3 \cdot 10^{-11}$ mol-cm$^{-2}$ was approximately four 4 times less than that obtained in a monocomponent monolayer formed by PQQ alone.

Figure 9A:
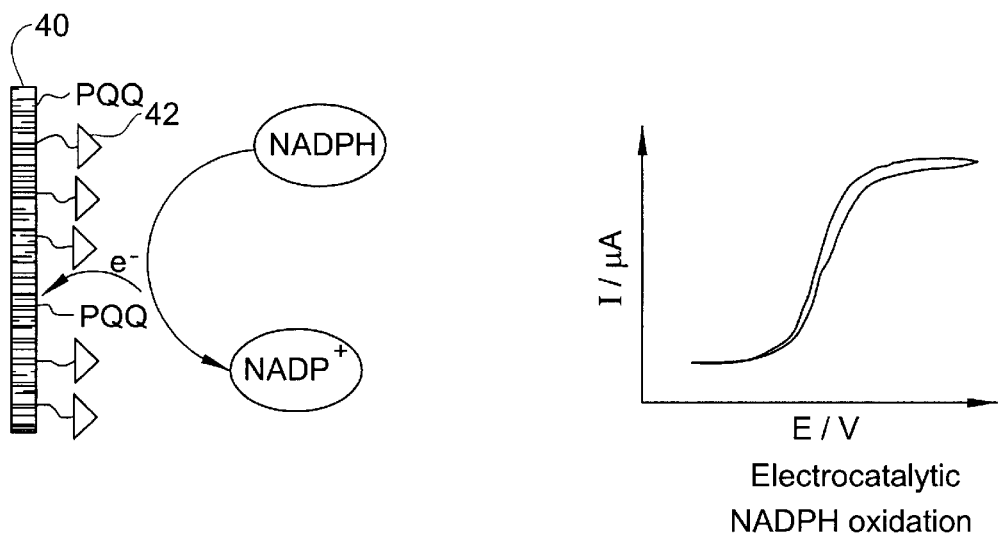
FIG. 9A illustrates the system and a schematic representation of the current response prior to exposure to an antibody.
Figure 9B:
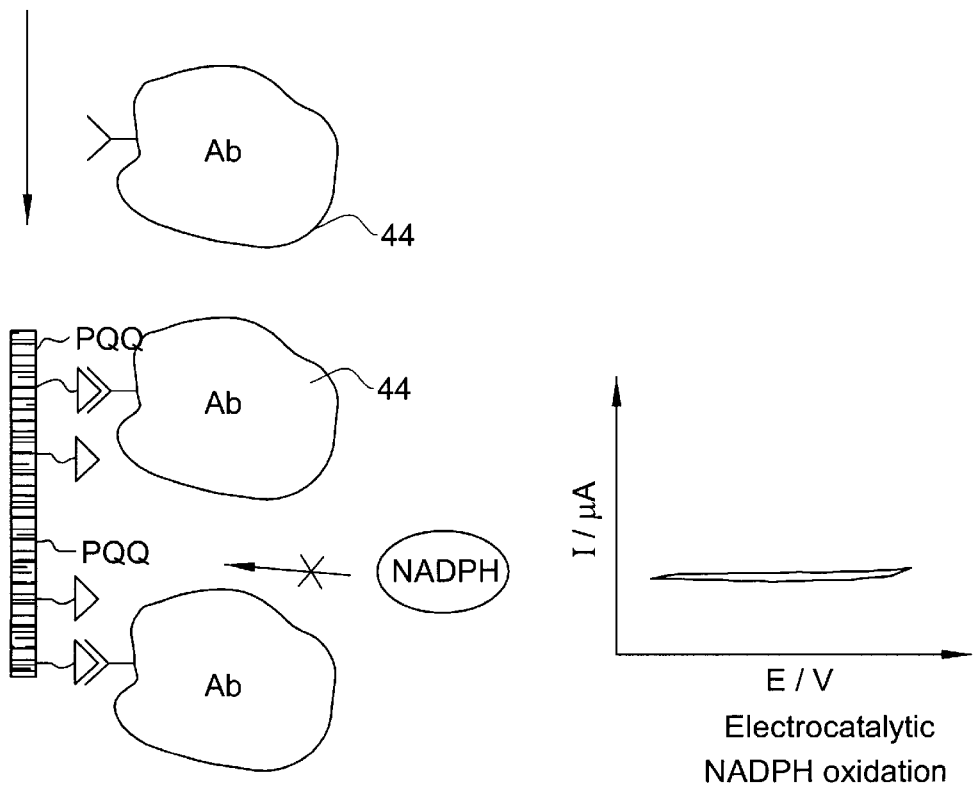
FIG. 9B illustrates the system and a schematic representation of the current response after exposure to antibodies and formations of pair complexes.

The function of the obtained electrode is illustrated in FIG. 9. Like components to those of FIG. 6 have been given the same reference numeral and the reader is referred to the description of FIG. 6 for a full explanation. In this example, in distinction to that illustrated in FIG. 6, the catalyst is PQQ and upon reduction becomes catalytically active in oxidizes NADPH into NADP+. NADPH is a relatively large molecule and the binding of antibody 44 to the immobilized antigen 42 blocks access of NADPH to the immobilized PQQ much more effectively than blocking of diffusion of $S_2O_8^{-2}$ in the example of FIG. 6.

Figure 10:
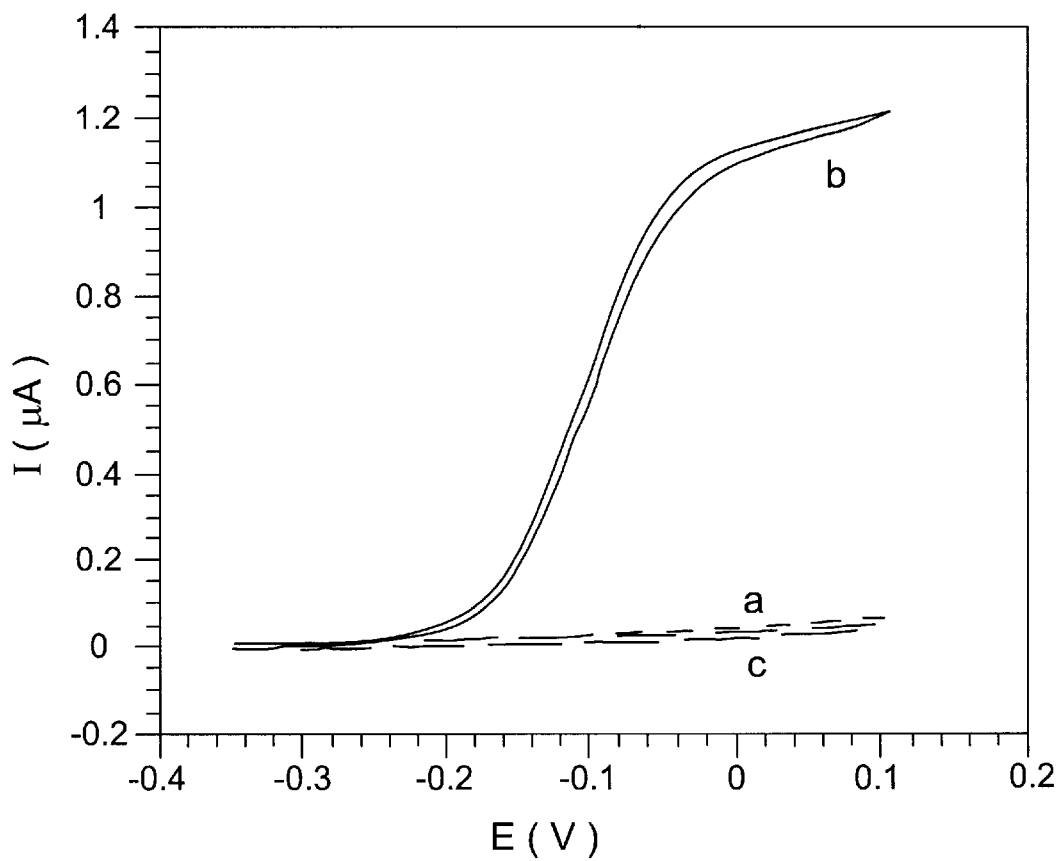
FIG. 10 shows cyclic voltammograms obtained with a modified gold electrode of a kind shown in FIGS. 8 and 9:
(a) in a control solution comprising 0.1 M Tris-HCl buffer, pH 7.0;
(b) in the presence of 10 mM NADPH and 20 mM calcium+2;
(c) in the same solution up to 20 mins. incubation of the modified electrodes in a solution comprising 50 mg/ml anti-dinitrophenol antibodies. Potential scan rate, 2 mv/s; temperature, 25° C.

Cyclic voltammograms obtained in the system are shown in FIG. 10 (all were performed in 25° C.). Curve b shows a cyclic voltammogram obtained in the presence of 10 mM NADPH (which is a substrate electrocatalytically oxidized by PQQ), 20 mM $Ca^{+2}$ (which is a promoter for electrooxidation of NADPH by PQQ), 0.1 M TRIS-HCl buffer, pH 7.0. Curve a in comparison was obtained in the absence of NADPH which demonstrates that the large cathodic current of curve b is a result of the electrocatalytic oxidation of NADPH. After soaking of the electrode for 20 min. in the same anti-DNP antibody solution as in Section 3.1, gave rise to a complete inhibition of the electrocatalytic oxidation of NADPH (curve c).

Figure 11:
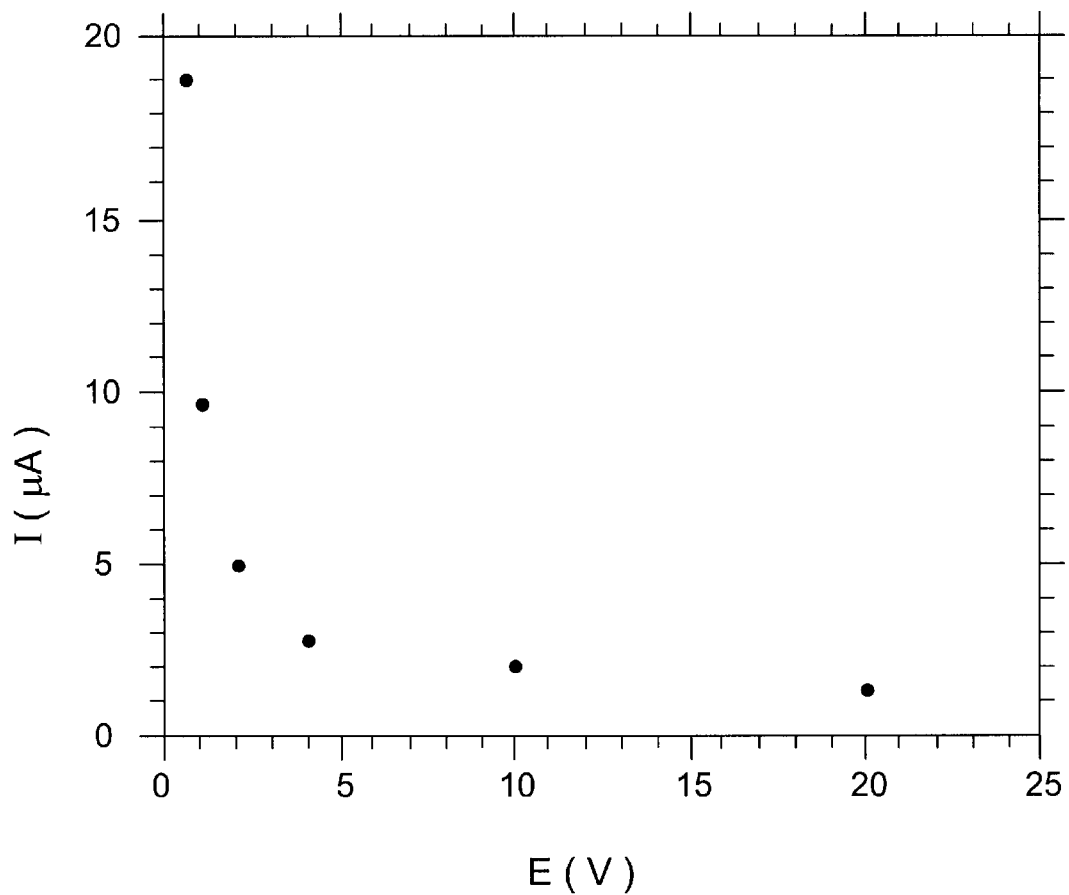
FIG. 11 shows the relation between the current and the antibody concentration in experiments conducted in a manner as in FIG. 10(c) with different antibody concentrations.

FIG. 11 shows that the anodic electrocatalytic current is dependent on the antibody concentration which approaches saturation upon increase in antibody concentration.

Figure 12:
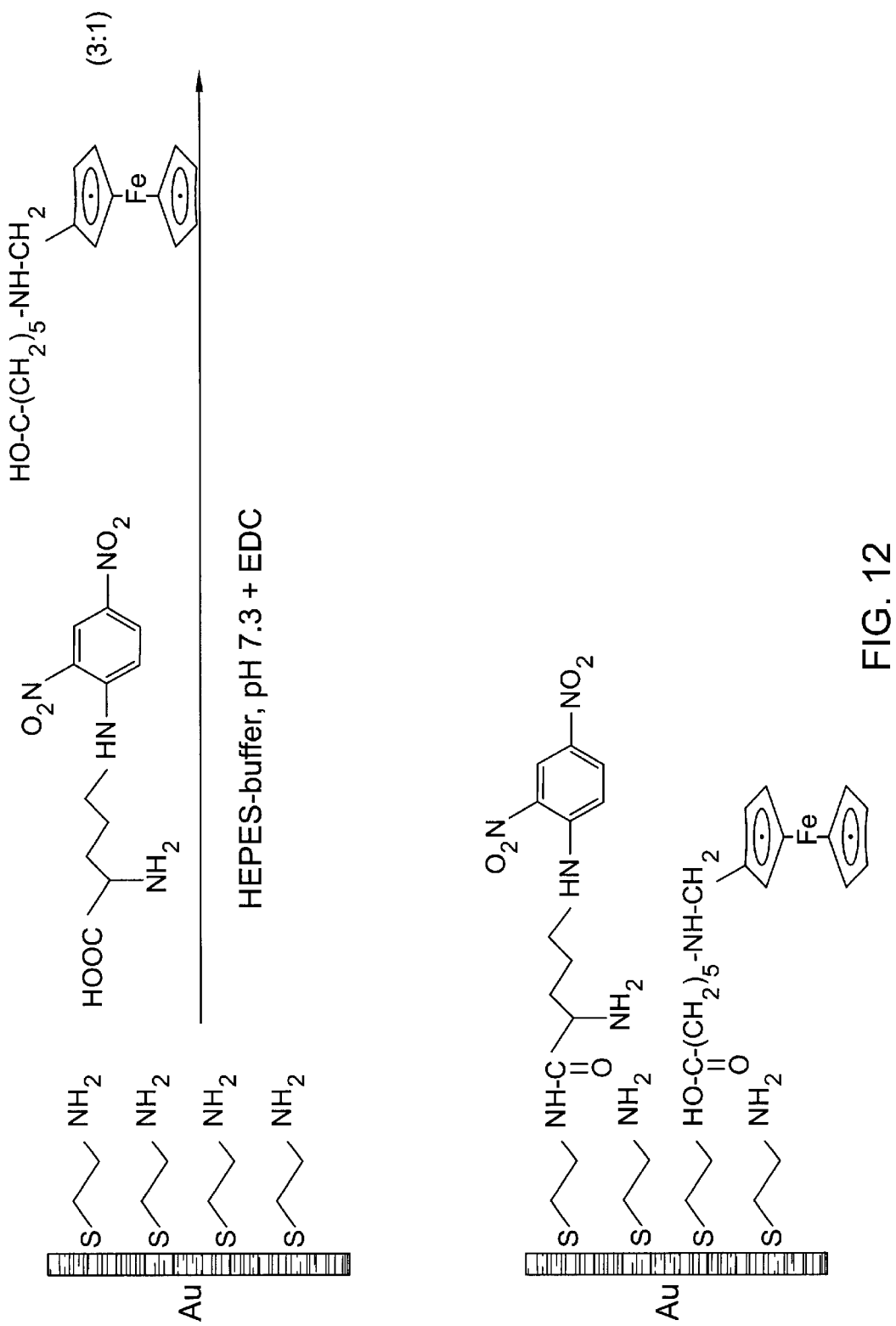
FIG. 12 illustrates the manner of modification of a cystamine covered gold electrode with a mixed monolayer consisting of 2,6-dinitrophenol lysine and a ferrocene group.

3.3 Dinitrobenzene derivative as an antigen and ferrocene unit as an electron transfer mediator A gold electrode modified so as to have a cystamine monolayer was soaked for 3 hours in a 0.01 M HEPES buffer solution, pH 7.3, containing 3 mM 2,6-dinitrophenol lysine (Aldrich) (as an antigen), 1 mM, a ferrocene carboxylic derivative having a long spacer between the ferrocene unit and carboxylic group (as an electron transfer mediator) and 10 mM 1-ethyl-3-(3-dimethylaminopropyl) carbodiimide (EDC, Aldrich) serving as a coupling reagent. Then the modified electrode was thoroughly rinsed with water to remove from its surface uncoupled physically adsorbed components. The modification scheme is illustrated in FIG. 12. A cyclic voltammogram was taken in the potential window from −0.1 V to +0.55 V with a potential scan rate 0.1 V s$^{-1}$ and the electrochemically reversible redox process of the immobilized ferrocene was used for determination of its surface density on the electrode surface. The obtained value of about $2.5 \cdot 10^{-11}$ mol·cm$^{-2}$ was approximately 4 times less than that obtained with a monocomponent monolayer formed by ferrocene only.

Figure 13A:
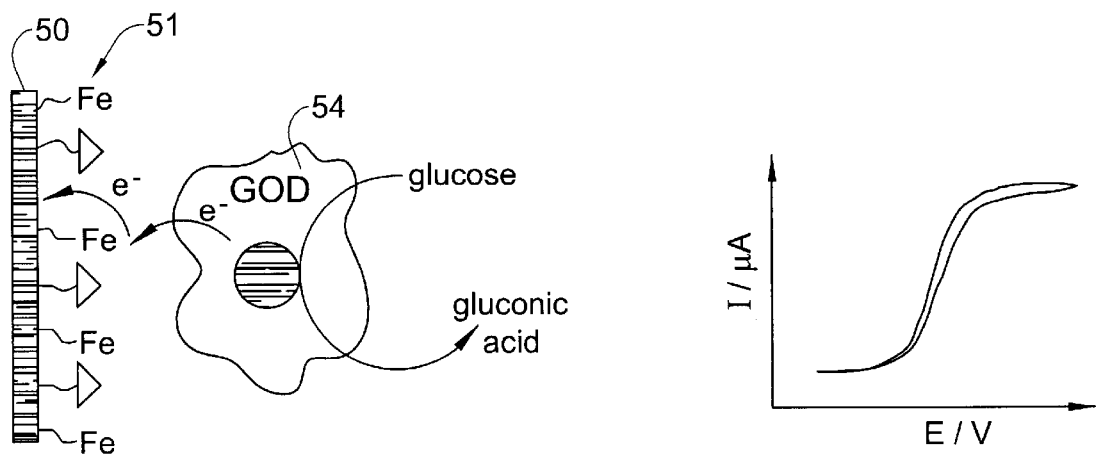
FIG. 13A illustrates the system and a schematic representation of the current response prior to exposure of the electrode to antibodies.
Figure 13B:
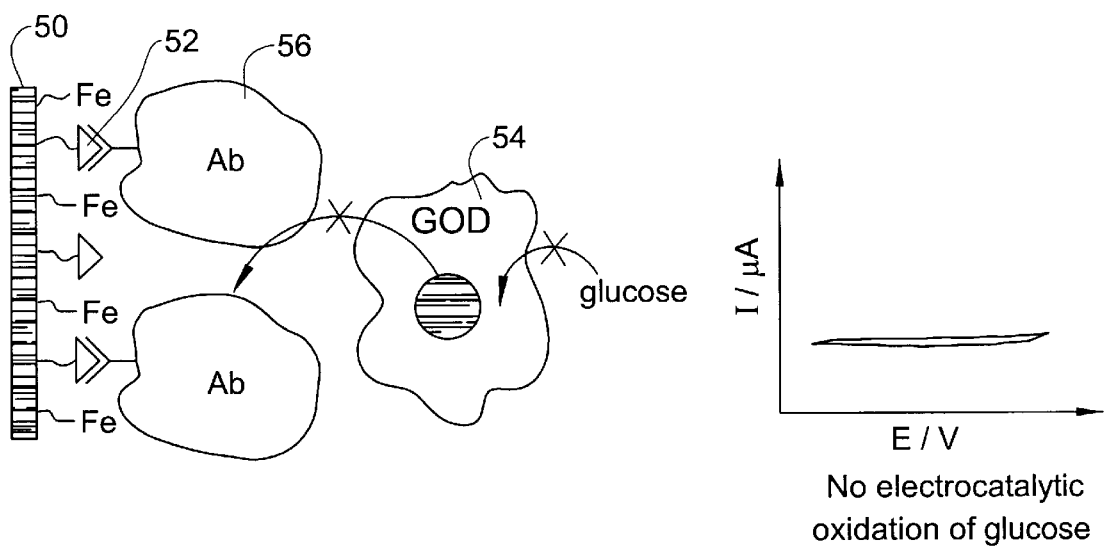
FIG. 13B illustrates the system and a schematic representation of the current response after exposure to antibodies and formation of pair complexes.

Reference is now being made to FIG. 13 illustrating a system comprising the above electrode. The system comprises an electrode 50 having an immobilized layer 51 comprising immobilized ferrocene molecules and antigens 52. The system further comprises a glucose oxidase (GOD) 54 which can catalyze a reaction in which glucose is oxidized to yield gluconic acid. Under normal conditions the GOD can approach the electrode whereby transfer of electrons between the GOD and the first redox molecule (the immobilized ferrocene) is possible, and upon such transfer the GOD catalyzes the oxidizing reaction, and there is a relatively large electrical response as shown in the schematic cyclic voltammogram shown in the right.

Figure 13C:
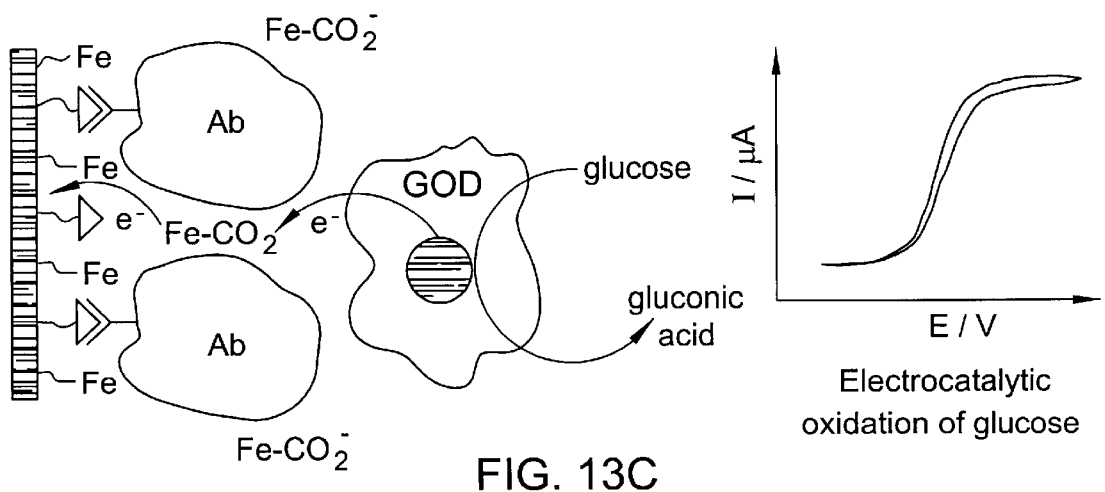
FIG. 13C illustrates the function of electrical response as in FIG. 13A upon addition of free, i.e. non-immobilized ferrocene monocarboxylic acid

Upon binding of antibodies 56 to antigens 52, the access of the GOD molecules to the immobilized ferrocene molecules is blocked and consequently there is no electron transfer and no oxidation of glucose. This gives rise to a very small electrical response as represented schematically in the cyclic voltammogram shown in the right. The electron transfer chain can be restored by adding free ferrocene monocarboxylic acid molecules to the system as shown in FIG. 13C.

Figure 14:
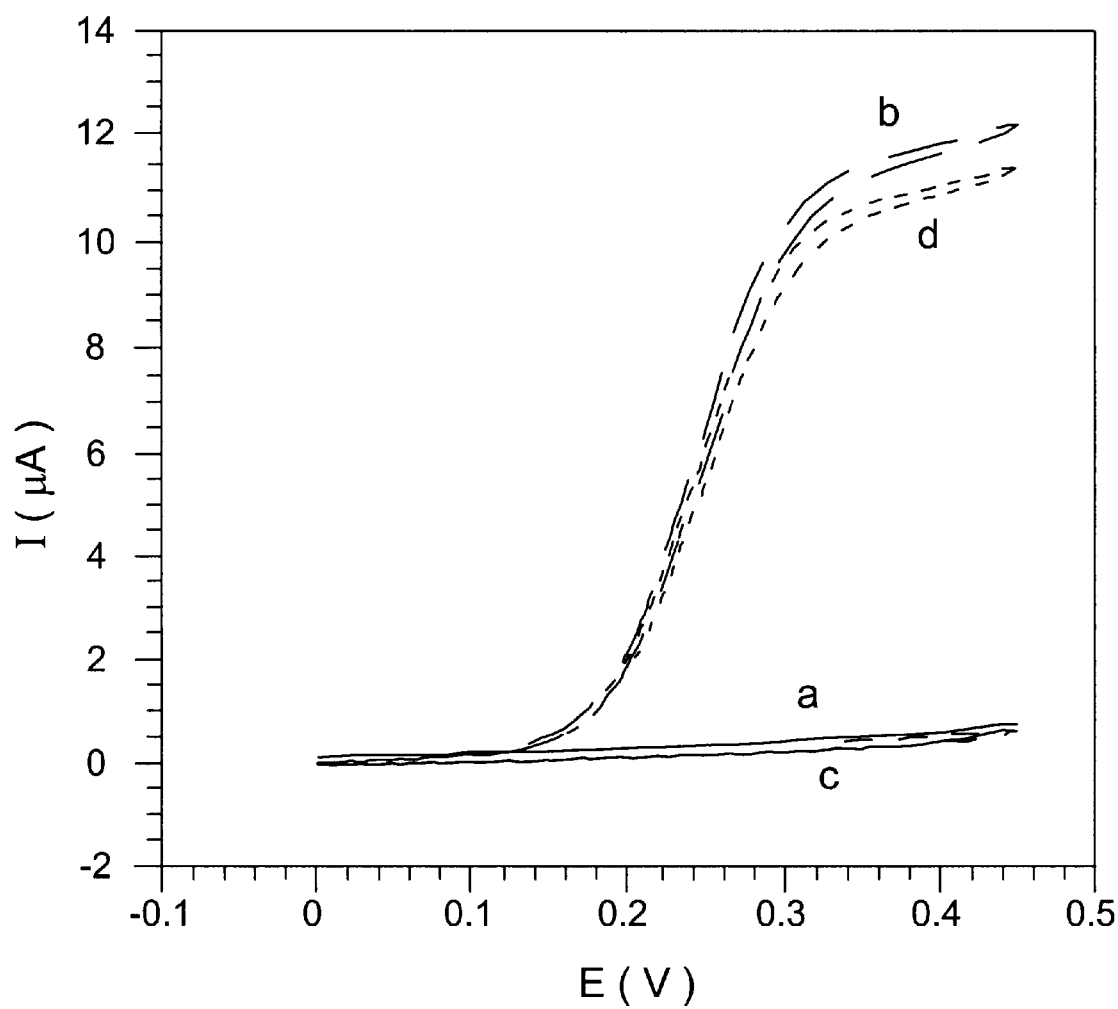
FIG. 14 shows cyclic voltammograms obtained with a modified gold electrode of a kind shown in FIGS. 12 and 13:
 (a) in a control solution comprising 0.01 M phosphate buffer, pH 7.0;
 (b) in the same solution comprising also 5 mg/ml GOD and 50 mM glucose;
 (c) in the same solution after 20 mins. incubation of the modified electrode in a solution comprising 50 mg/ml anti-dinitrophenol antibodies;
 (d) as in (c), but with the addition of 0.5 mM ferrocene mono-carboxylic acid. Potential scan rate, 2 mv/s; temperature, 35°.

Cyclic voltammograms obtained in such a system (at 35° C.) are shown in FIG. 14. The cyclic voltammogram of curve b was obtained in the presence of 5 mg/ml glucose oxidase (GOD), from *Aspergillus niger*, EC 1.1.3.4, Sigma) and 50 mM glucose (a substrate electrocatalytically oxidized by GOD), 0.01 M phosphate buffer and 0.1 M $Na_2SO_4$. Curve a, in comparison, was taken in the absence of glucose and the very large increase of the anodic current is a result of the electrocatalytically oxidation of glucose by the GOD. This biocatalytic process occurs only in the presence of ferrocene units which facilitate electron transfer from the solubilized GOD to the electrode. When the modified electrode was soaked for 20 min. in a solution containing 50 mg/ml anti-DNP antibodies, there was essentially a total elimination of the anodic current (curve c) being an indication of the fact that the electrocatalytic oxidation of glucose is completely blocked by the antibody monolayer. As can be seen from curve d, upon addition of solubilized ferrocene monocarboxylic acid (Aldrich) the concentration of $5 \cdot 10^{-3}$, which then serves as a diffusionally mobile electron transfer mediator, the anodic current was almost restored to normal.

Figure 16:
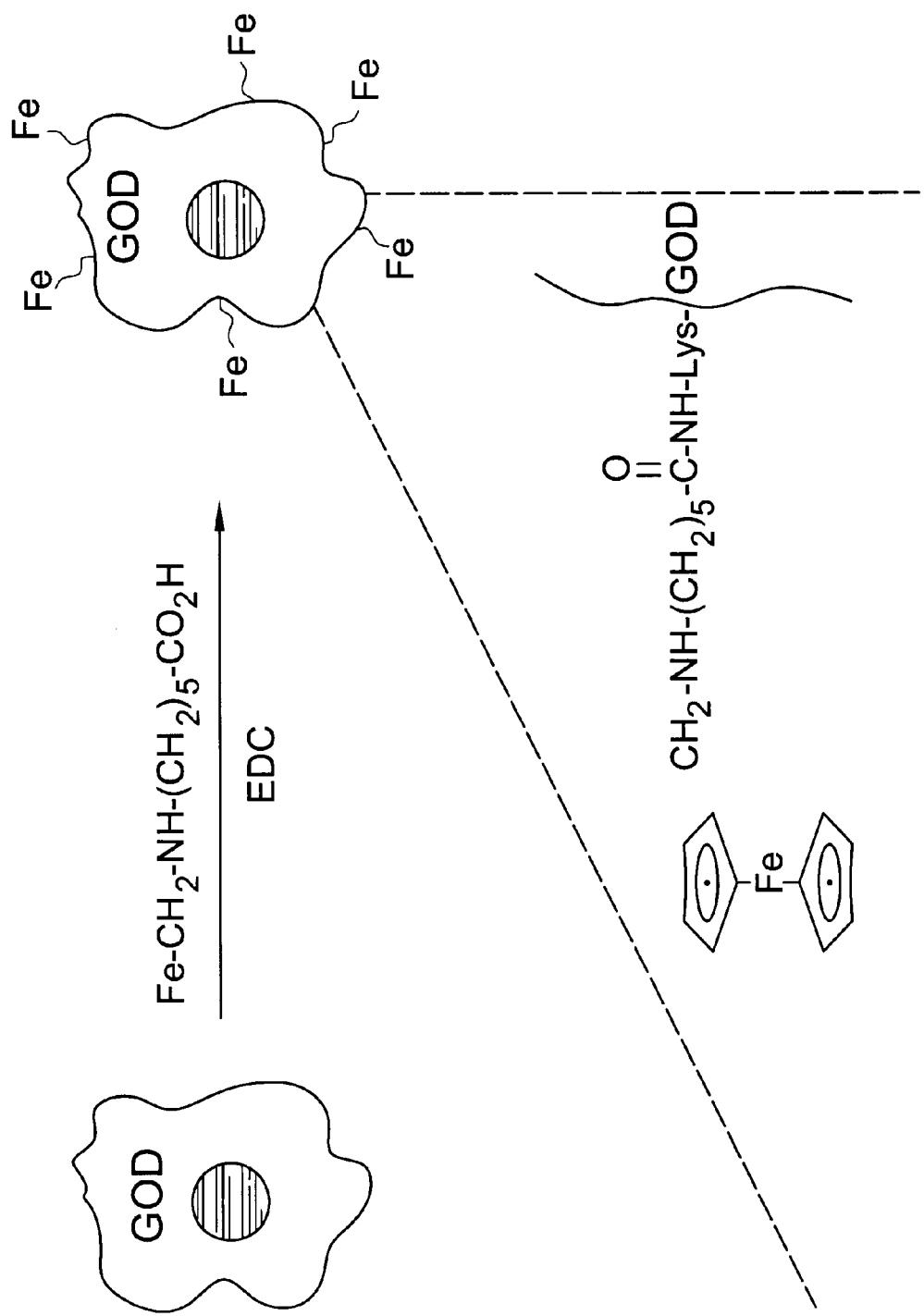
FIG. 16 illustrates the manner of "electrically wiring" of the enzyme glucose oxidase (GOD) with a plurality of randomly located ferrocene groups.

4. ELECTRODES WITH A MONOLAYER CONSISTING OF AN ANTIGEN COMPONENT ONLY 4.1 Dinitrobenzene derivative as a monolayer immobilized antigen on an electrode surface and glucose oxidase modified with many ferrocene units as a solubilized biocatalytic probe A gold electrode modified so as to have a cystamine monolayer was soaked for 3 hours in a 0.01 M HEPES buffer solution, pH 7.3, containing 3 mM 2,6-dinitrophenol lysine (Aldrich) (as an antigen) and 10 mM 1-ethyl-3-(3-dimethylaminopropyl) carbodiimide (EDC, Aldrich) (as a coupling reagent). Then the modified electrode was thoroughly rinsed with water to remove from its surface uncoupled physically adsorbed components. The modification scheme is illustrated in FIG. 15. Glucose oxidase (GOD) was covalently modified with many ferrocene units by coupling of the amino groups of the lysine residuals with the ferrocene carboxylic derivative in the presence of a carbodiimide coupling reagent (EDC), then the modified enzyme was purified according to a known procedure. The enzyme modification scheme and the modified enzyme structure are illustrated in FIG. 16.

Figure 17A:
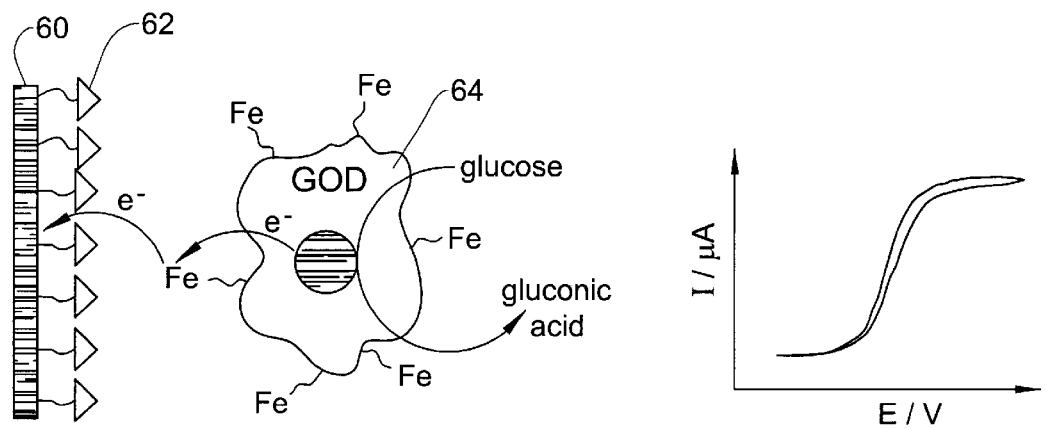
FIG. 17A illustrates the system and a schematic representation of the current response prior to exposure to antibodies.
Figure 17B:
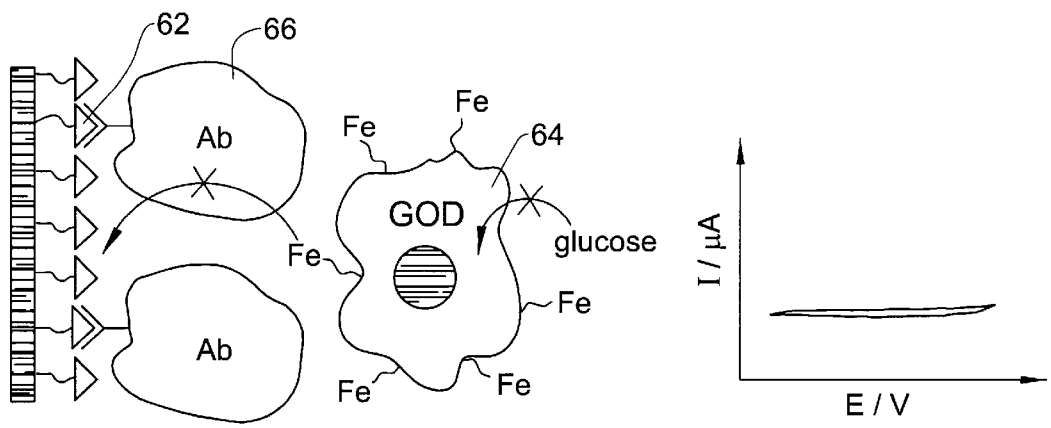
FIG. 17B illustrates the system and a schematic representation of the current response after exposure to antibodies and formation of pair complexes.
Figure 17C:
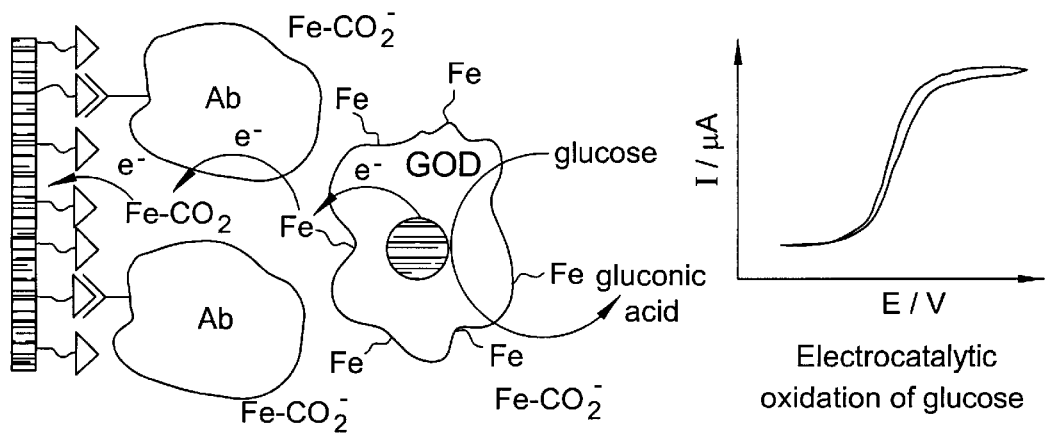
FIG. 17C illustrates the restoration of the electrical response of FIG. 17A after addition of free ferrocene monocarboxylic acid.

The function of a system comprising the above electrode is illustrated in FIG. 17. Similarly as in FIG. 13, under regular conditions, modified enzyme 64 can approach the surface of an electrode 60 and electrons can transfer between the redox center of the enzyme to the ferrocene groups bound thereto and from there to the surface of the electrode, thus yielding glucose oxidation. When antibodies 66 bind to immobilized antigens 62 then modified enzyme 64 cannot come close to the surface of the electrode and accordingly the electrical response of the system is essentially totally eliminated. Electrical transfer chain can be restored by the addition of 3 ferrocene carboxylic acid molecules into the medium as shown in FIG. 17C.

Figure 18:
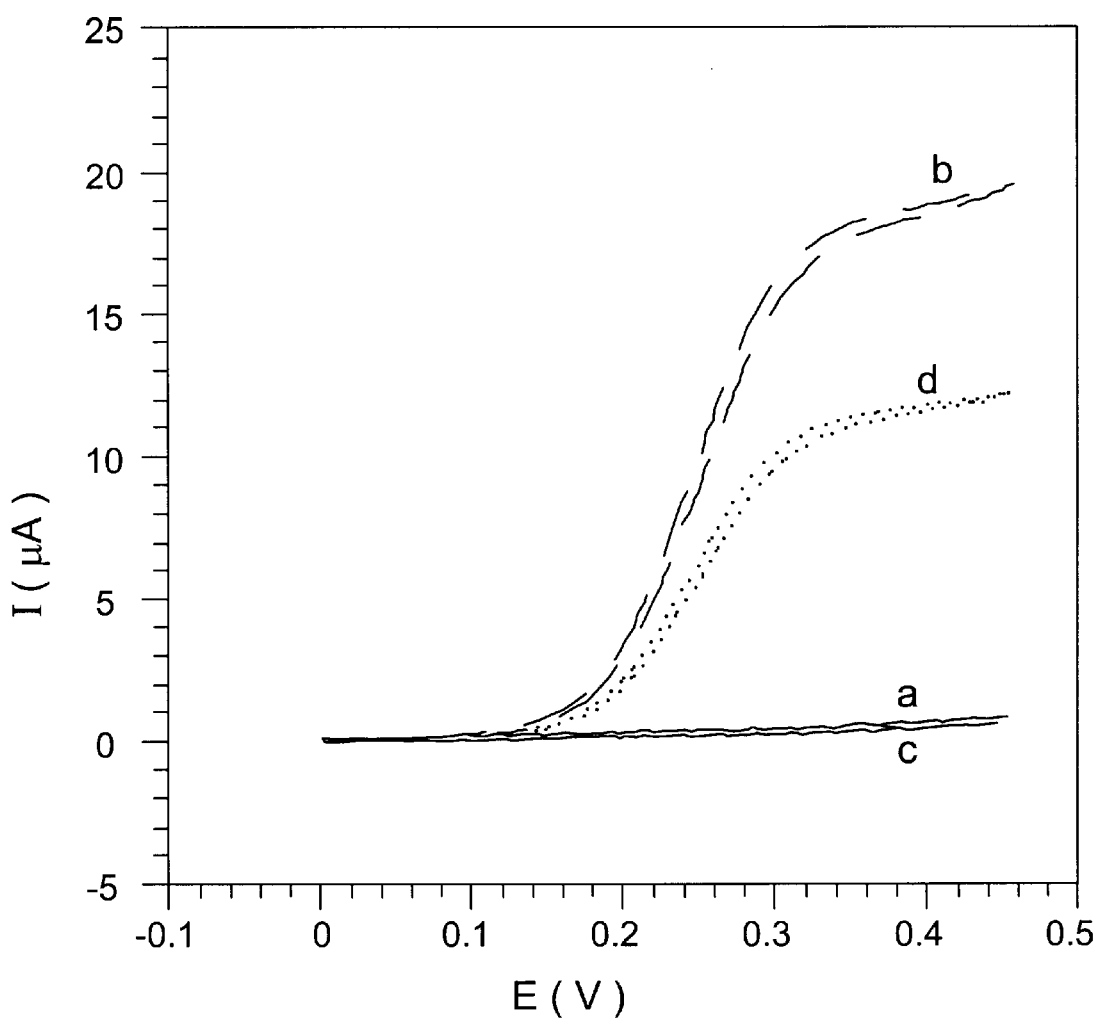
FIG. 18 illustrates cyclic voltammograms obtained with a modified gold electrode of a kind shown in FIG. 17:
 (a) in a control solution comprising 0.01 M phosphate buffer, pH 7.0;
 (b) in the same solution comprising 5 mg/ml "wired" GOD and 50 mM glucose;
 (c) in the same solution after 20 mins. incubation of the modified electrode in a solution comprising 50 mg/ml anti-dinitrophenol antibodies;
 (d) same electrode in solution as in (c) but with the addition of 0.5 mM ferrocene monocarboxylic acid. Potential scan rate, 2 mv/s; temperature, 35° C.

FIG. 18 shows cyclic voltammograms obtained in the system illustrated in FIG. 17. All cyclic voltammograms were done at 35° C. Cyclic voltammograms were taken in the presence of 5 mg/ml ferrocene modified GOD, 0.01 M phosphate buffer, pH 7.0 and 0.1 M $Na_2SO_4$. Under such conditions there was essentially no anodic current (curve a). Once glucose was added (50 mM) there was a very large increase in the anodic current (curve b). After soaking of the electrode in an anti-DNP antibody solution (50 mg/ml) for 20 min., followed by rinsing with water, the anodic current was essentially totally eliminated (curve c). The electrocatalytic process could be restored, to some extent, by the addition of $5 \cdot 10^{-3}$ M free ferrocene monocarboxylic acid (curve d).

Figure 19:
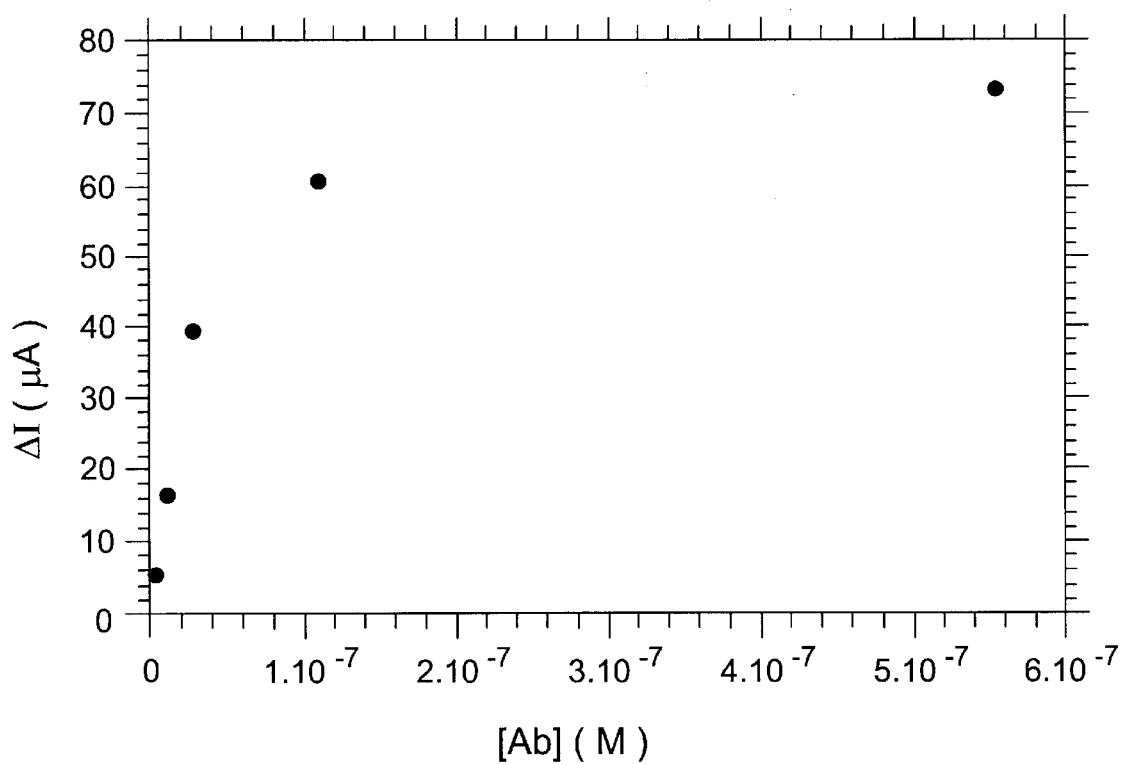
FIG. 19 shows changes in electrocatalytic currents in experiments performed as in FIG. 15 (c), following 6 min. incubation in an antibody solution comprising various antibody concentrations.

FIG. 19 shows results from various experiments conducted as above with different antibody concentrations and as can be seen, change in anodic current depends on the antibody concentration.

4.2 Fluorescein derivative as a monolayer immobilized antigen on an electrode surface and glucose oxidase modified with many ferrocene units as a solubilized biocatalytic probe A gold electrode modified so as to have a cystamine monolayer was soaked overnight in the 0.1 M phosphate buffer, pH 8.9, containing 5 mM fluorescein isothiocyanate (isomer 1, Aldrich) (as an antigen). The covalent attachment of fluorescein units to the cystamine monolayer was a result of a spontaneous reaction between the surface amino groups and isothiocyanate groups giving thioamide bonds. Then the modified electrode was thoroughly rinsed with water to remove from its surface uncoupled physically adsorbed components. The antigen modified electrode was used for electrochemical immunoassay as it is described in Section 4.1 with only one difference in that the applied antibody was anti-fluorescein (FITC) monoclonal antibody (Sigma). All electrochemical measurements were done at 35° C. The obtained results are very similar to the described above in the previous example 4.1.

Figure 20:
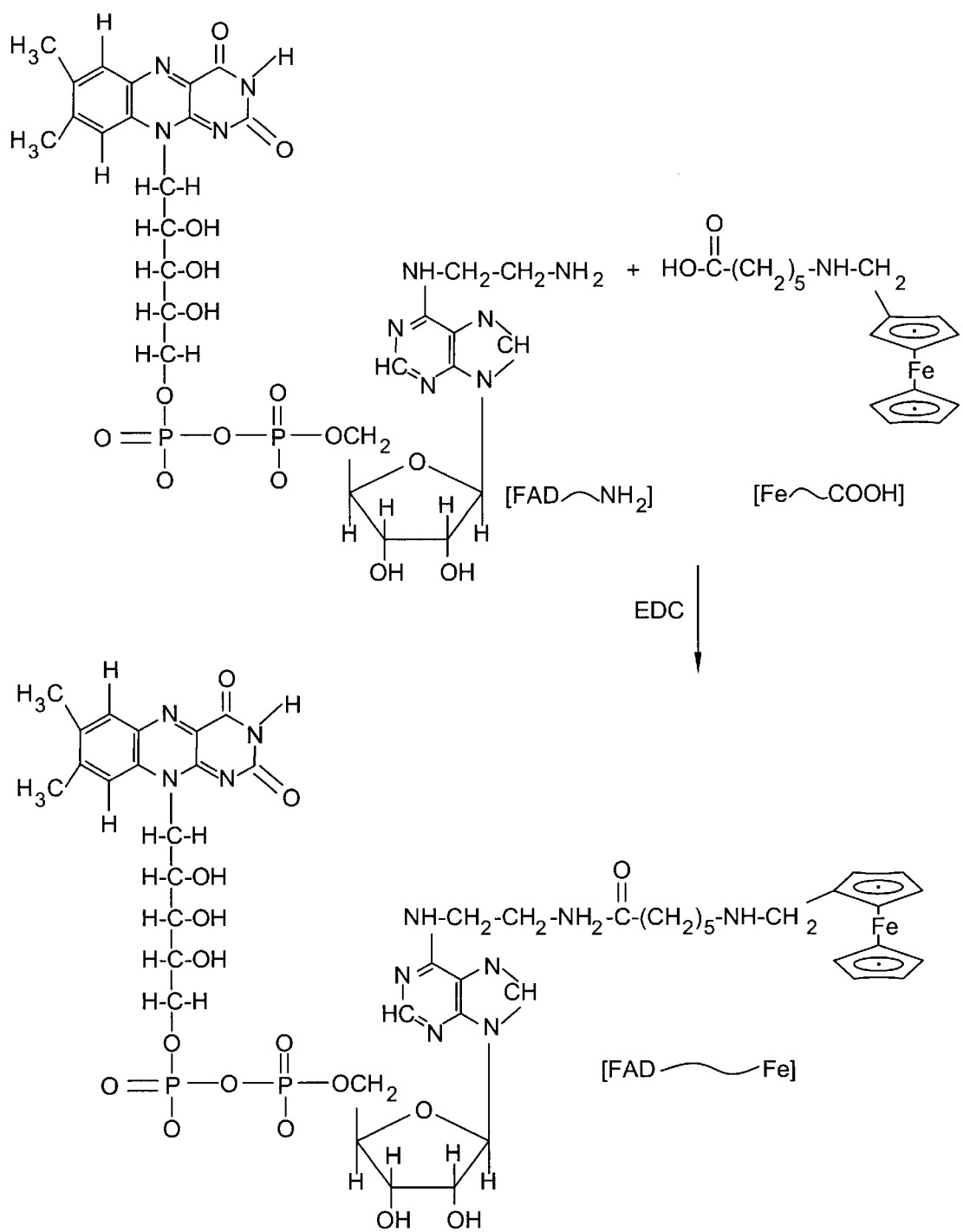
FIG. 20 illustrates the last synthetic step in the preparation of an FAD analog covalently-linked to a ferrocene group (FAD-Fc).
Figure 21:
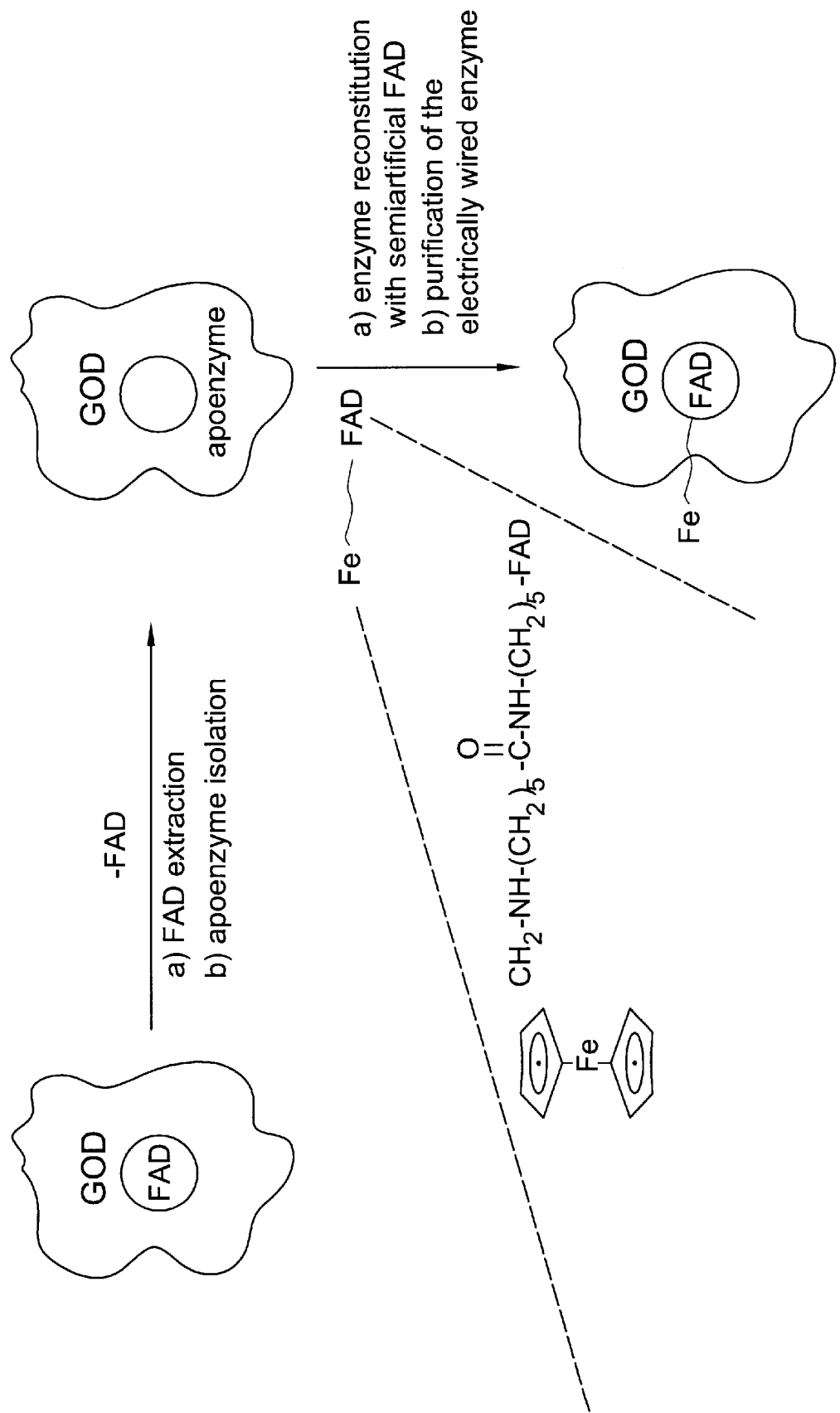
FIG. 21 illustrates the preparation of a GOD apoenzyme and its reconstitution with the FAD-Fc obtained as shown in FIG. 20.

4.3 Dinitrobenzene derivative as a monolayer immobilized antigen on an electrode surface and glucose oxidase reconstituted with semiartificial FAD covalently linked to ferrocene unit A gold electrode modified so as to have a cystamine monolayer was further modified with 2,6-dinitrophenol lysine as it is described above. A GOD apoenzyme was obtained by known biochemical procedure[26]. A semiartificial FAD ($N^6$-(2-aminoethyl)-FAD) containing a primary amino group separated from the FAD molecule with two methylene groups was covalently linked with a ferrocene carboxylic derivative using a carbodiimide coupling reagent producing an amide bond between the two components. The FAD derivative covalently linked with the ferrocene unit (FAD-Fc) was used to reconstitute the GOD apoenzyme[27]. The last synthetic step in preparation of the FAD-Fc, the GOD apoenzyme preparation and its reconstitution with FAD-FC are illustrated in FIGS. 20 and 21, respectively.

Figure 22A:
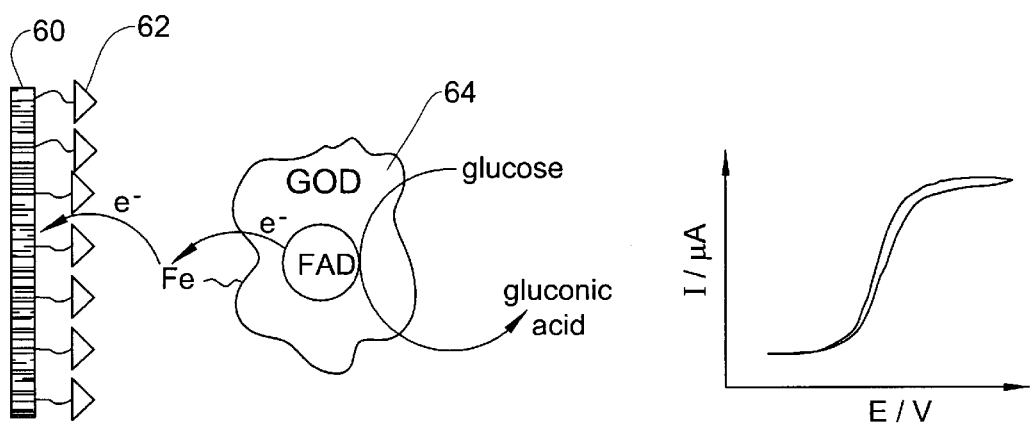
FIG. 22A illustrates the function of the system in a schematic representation of the current response prior to exposure to an antibody.
Figure 22B:
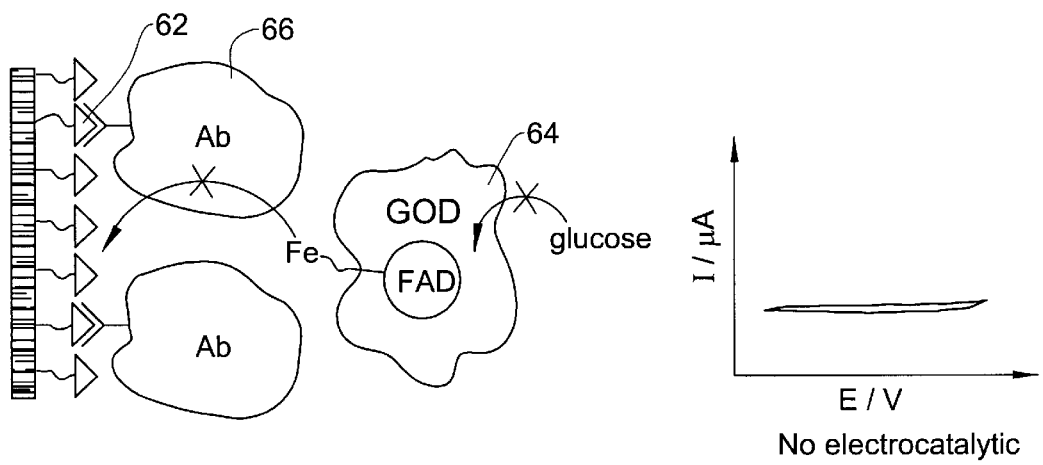
FIG. 22B illustrates a system and a schematic representation of the current response after exposure of the antibody and the formation of immobilized pair complexes.
Figure 22C:
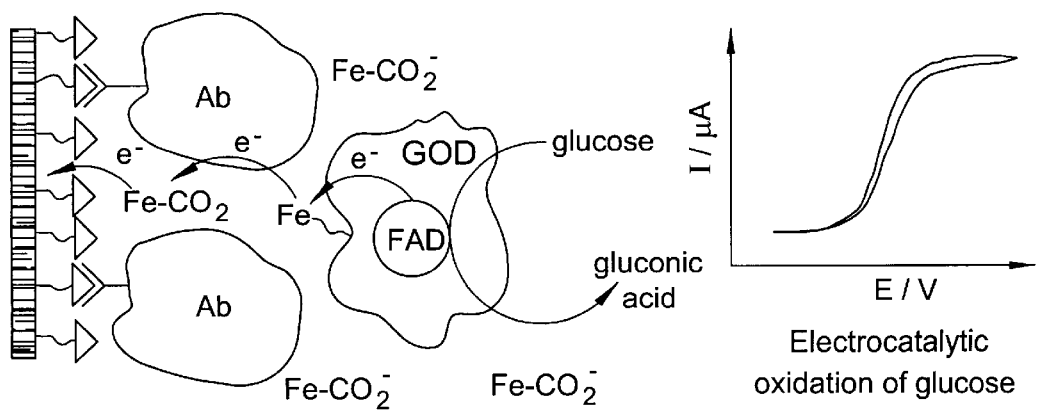
FIG. 22C illustrates the restoration of the electrical response upon addition of free ferrocene molecules.

The system comprising this electrode is illustrated schematically in FIG. 22. The system is basically similar to that shown in FIG. 17 and accordingly like numbers were used to designate like components. The only difference is in that the ferrocene group, rather than being bound to the enzyme, is bound here to the FAD derivative.

Figure 23:
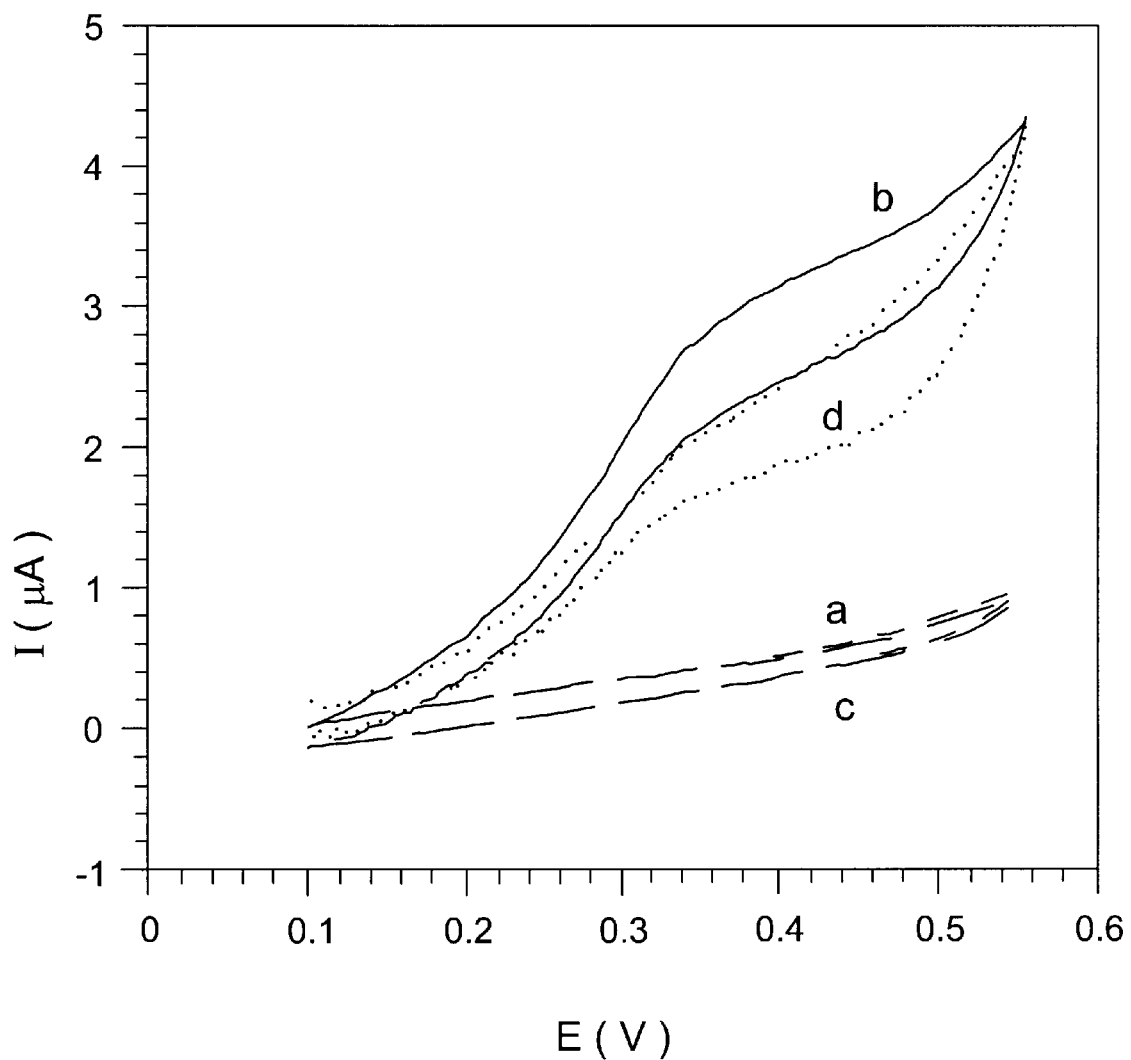
FIG. 23 shows cyclic voltammograms obtained with a modified electrode of the kind shown in FIG. 22:
 (a) in a background solution comprising 0.01 M phosphate buffer, pH 7.0;
 (b) in the same solution with 5 mg/ml GOD reconstituted with FAD-Fc and 50 mM glucose;
 (c) in the same solution as in (b) after 20 mins. incubation of the modified electrode in a solution comprising 50 mg/ml anti-dinitrophenol antibody;
 (d) as in (c) but with the addition of 0.5 mM ferrocene mono-carboxylic acid. Potential scan rate, 2 mv/s; temperature, 35° C.

Cyclic voltammogram results obtained under similar conditions as those described in Section 4.2 above are shown in FIG. 23. As can be seen, the results are qualitatively similar to those of FIG. 18: essentially no current in the absence of glucose (curve a), a very large increase in the anodic current following addition of glucose (curve b), essentially total elimination of the current following support of the electrode to anti-DNP antibodies (curve c) and then restoration of the electrical response following addition of free ferrocene monocarboxylic acid molecules (curve d).

Figure 24A:
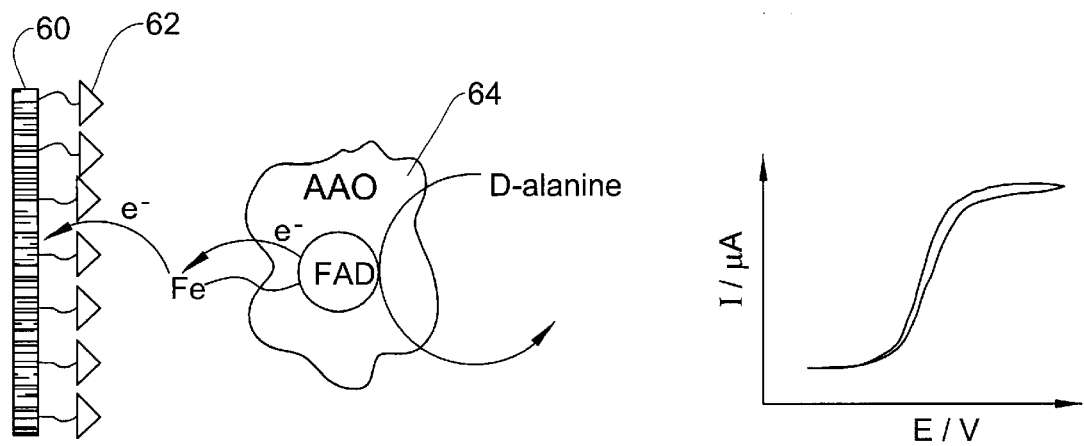
FIG. 24A illustrates the system and a schematic representation of the current response prior to exposure of the electrode to an antibody.
Figure 24B:
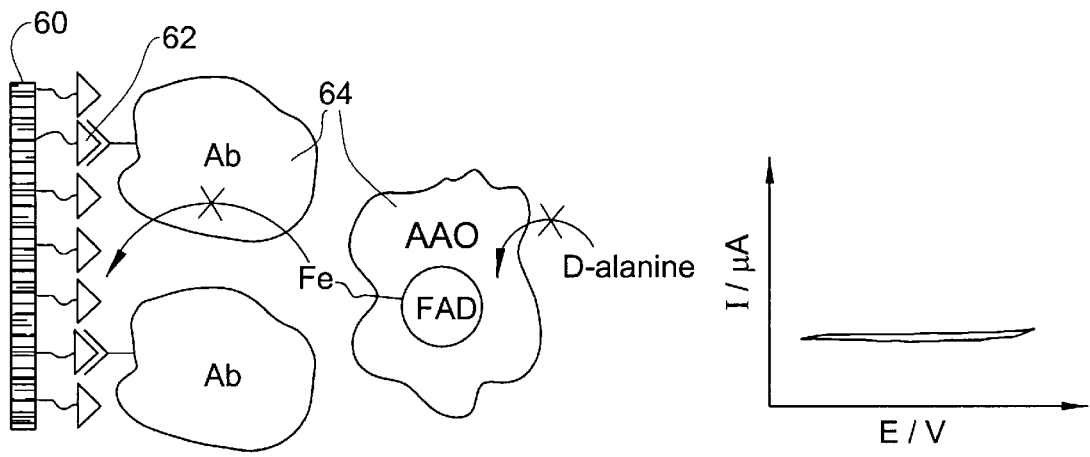
FIG. 24B illustrates the system and a schematic representation of the current response after exposure to an antibody and formation of immobilized pair complexes.
Figure 24C:
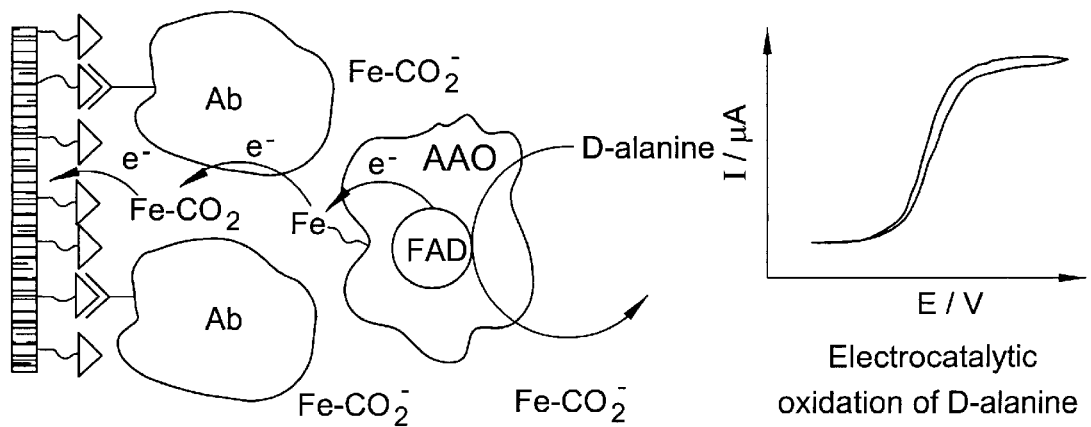
FIG. 24C illustrates the restoration of the electrical response obtained in FIG. 24A after addition of free ferrocene monocarboxylic acid.
Figure 25:
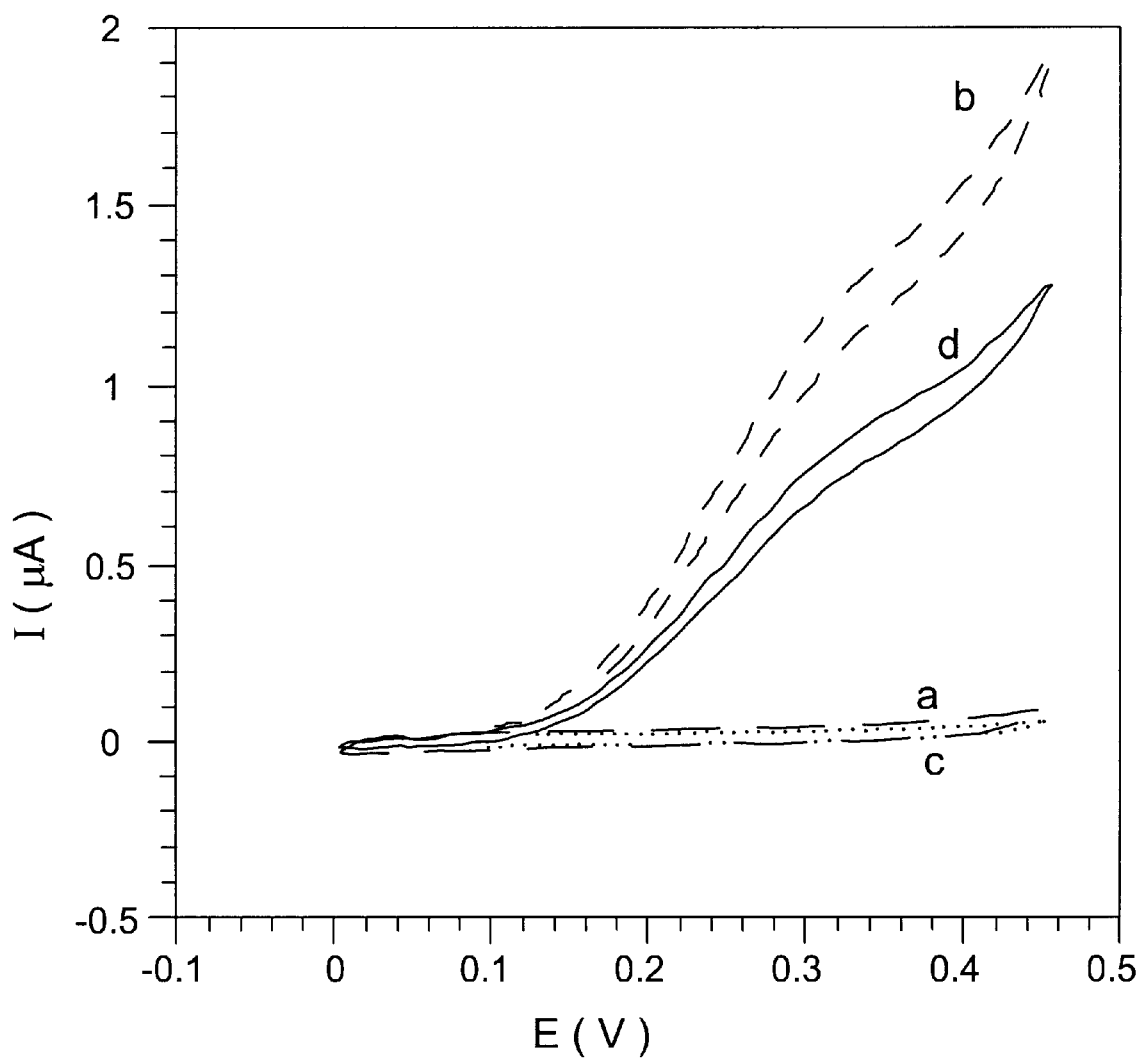
FIG. 25 shows a cyclic voltammogram obtained in a system illustrated in FIG. 24:
 (a) in a control solution comprising 0.01 M phosphate buffer, pH 7;
 (b) as in (a) with the addition of 5 mg/ml AAO reconstituted with FAD-Fc and 50 mM D-alanine;
 (c) the same solution as in (b), but following incubation of the modified electrode in a solution comprising 50 mg/ml anti-dinitrophenol antibody;
 (d) same electrode and solution as in (c) but with the addition of 0.5 mM ferrocene monocarboxylic acid. Potential scan rate, 2 mv/s; temperature,35° C.

4.4 Dinitrobenzene derivative as a monolayer immobilized antigen on an electrode surface and amino acid oxidase reconstituted with semiartificial FAD covalently linked to ferrocene unit The present example is almost identical to that under 4.3 with the only difference being in that D-amino acid oxidase (AAO, EC 1.4.3.3, Sigma) reconstituted with FAD-Fc and the corresponding substrate (D-alanine) were used instead of the reconstituted GOD and glucose, respectively. The system which is essentially similar to that of FIG. 22 is illustrated in FIG. 24 (the same reference numerals as in FIG. 22 are used in this figure). Results obtained in this system are illustrated in FIG. 25 and are qualitatively similar to those of FIG. 23: background (curve a), upon addition of glucose (curve b), following exposure to anti-DNP antibodies (curve c) and after addition of soluble ferrocene monocarboxylic acid (curve d).

What is claimed is:

1. An electrochemical system for determining the presence of an analyte in a liquid medium, the system comprising:

redox molecules comprising at least one first redox molecule and at least one second redox molecule, said first molecule transferring electrons between said electrode and said second molecule; and an electrode having immobilized thereon a member of a recognition pair, said analyte being the other member of said pair, whereby presence of said analyte in the medium results in formation of one pair complex, being a complex between the immobilized member and said analyte;

formation of said pair complex said pair complex inhibiting the electron transfer and a change in the system's electrical response as a result thereto, indicating presence of said analyte in medium.

2. A system according to claim 1, wherein said first redox molecule is a catalytically active molecule which upon transfer of electrons to the second redox molecule induces a reaction in which said second redox molecule is converted to one or more products.

3. A system according to claim 1, wherein said first redox molecule is an electromediator and said second redox molecule is a catalytically active molecule, the system further comprises a third redox molecule which is converted by said second redox molecule into a product.

4. A system according to claim 2, wherein said first redox molecule is immobilized on the electrode.

5. A system according to claim 2 or 3, wherein the first and the second redox molecules are complexed to one another.

6. An electrochemical method for determining presence of an analyte in a liquid medium, the method comprising:

a) providing an electrode having immobilized thereon one member of a recognition pair, said analyte being the other member of said pair; a first redox molecule not immobilized on the electrode, said first redox molecule being capable of transferring electrons between the electrode and a second redox molecule;

b) contacting said electrode with said liquid medium, whereby the presence therein of said analyte results in the formation of pair complexes, said pair complexes being complexes between the immobilized member and said analyte, on the surface said electrode;

c) contacting said electrode with said second redox molecule, and also with said first redox molecule; and d) charging the electrode whereby electron transfer between said electrode and said second redox molecule by the mediation of said first redox molecule gives rise to an electrical response, a change in the electrical response following exposure of the electrode to said medium indicating the presence of said analyte in the medium.

7. A method according to claim 6, wherein said first redox molecule is a catalytically active molecule which upon transfer of electrons to the second redox molecule induces a reaction in which said second redox molecule is converted to one or more products.

8. A method according to claim 6, wherein said first redox molecule is an electromediator and said second redox molecule is a catalytically active molecule, which catalyzes a reaction in which a third redox molecule is converted into a product, and step (c) comprises contacting said electrode also with said third redox molecule.

9. A method according to claim 6, wherein said first redox molecule is immobilized on the electrode.

10. A method according to claims 6, wherein said first redox molecule and said second redox molecule are complexed to one another.

* * * * *